(12) United States Patent
Rath et al.

(10) Patent No.: US 10,371,604 B2
(45) Date of Patent: Aug. 6, 2019

(54) BIOLOGICAL SAMPLE PREPARATION FOR TESTING

(71) Applicant: LIFE TECHNOLOGIES CORPORATION, Carlsbad, CA (US)

(72) Inventors: Mousumi Rath, San Ramon, CA (US); Mark Shannon, San Francisco, CA (US); Jason La, San Francisco, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 212 days.

(21) Appl. No.: 15/233,801

(22) Filed: Aug. 10, 2016

(65) Prior Publication Data

US 2017/0045428 A1 Feb. 16, 2017

Related U.S. Application Data

(60) Provisional application No. 62/203,311, filed on Aug. 10, 2015, provisional application No. 62/303,227, (Continued)

(51) Int. Cl.
*G01N 1/04* (2006.01)
*C12Q 1/6806* (2018.01)
(Continued)

(52) U.S. Cl.
CPC ............ *G01N 1/04* (2013.01); *C12Q 1/6806* (2013.01); *G01N 1/286* (2013.01); *G01N 1/2813* (2013.01);
(Continued)

(58) Field of Classification Search
None
See application file for complete search history.

(56) References Cited

U.S. PATENT DOCUMENTS 5,859,699 A 1/1999 Baer et al.
5,985,085 A * 11/1999 Baer .................... G01N 1/2813
156/285

(Continued)

FOREIGN PATENT DOCUMENTS

EP 2395082 12/2011
WO WO-2017/027620 2/2017
WO WO-2017/027627 2/2017

OTHER PUBLICATIONS

PCT/US2016/046399, International Search Report and Written Opinion dated Nov. 4, 2016, 1-12.

(Continued)

*Primary Examiner* — Robert T. Crow

(57) ABSTRACT

In one embodiment, a method for processing a sample includes selecting a selected sample from a biological specimen, the selected sample being in contact with a first surface of a first substrate. The method also includes transferring the selected sample directly from the first surface to a container comprising an internal volume. The method also includes forming or providing a sample solution within the internal volume of the container by contacting the selected sample with a lysis mixture using a protocol. The method further includes performing an assay, experiment, or test on the sample solution while the sample solution disposed is within the internal volume of the container.

In another embodiment, a method for processing a sample includes providing a selected sample comprising one or more cells. The method also includes transferring the selected sample into an internal volume of a container. The method also includes contacting the selected sample with a lysis mixture using a protocol to provide a sample solution, wherein the protocol comprises heating the sample solution (Continued)

to a first temperature that is greater than 37 degrees Celsius and less than or equal to 75 degrees Celsius.

19 Claims, 22 Drawing Sheets

Related U.S. Application Data filed on Mar. 3, 2016, provisional application No. 62/341,563, filed on May 25, 2016.

(51) Int. Cl.
    *G01N 1/28*      (2006.01)
    *G01N 1/34*      (2006.01)
    *G01N 1/02*      (2006.01)
    *B01L 3/00*      (2006.01)

(52) U.S. Cl.
    CPC ..... *B01L 3/50825* (2013.01); *B01L 2300/042* (2013.01); *B01L 2300/046* (2013.01); *B01L 2300/0838* (2013.01); *G01N 1/34* (2013.01); *G01N 2001/028* (2013.01); *G01N 2001/045* (2013.01); *G01N 2001/284* (2013.01); *G01N 2001/2886* (2013.01)

(56) References Cited

U.S. PATENT DOCUMENTS

| | | | |
|---|---|---|---|
| 6,157,446 A | 12/2000 | Baer et al. | |
| 6,469,779 B2 | 10/2002 | Baer et al. | |
| 6,495,195 B2 | 12/2002 | Baer et al. | |
| 6,528,248 B2 | 3/2003 | Lossing et al. | |
| 6,690,470 B1 | 2/2004 | Baer et al. | |
| 6,887,703 B2 | 5/2005 | Baer et al. | |
| 7,049,558 B2 | 5/2006 | Baer et al. | |
| 7,075,640 B2 | 7/2006 | Baer et al. | |
| 7,229,595 B2 | 6/2007 | Richardson | |
| 7,456,938 B2 | 11/2008 | Malekafzall | |
| 7,473,401 B1 | 1/2009 | Baer | |
| 7,556,733 B2 | 7/2009 | Smith et al. | |
| 7,749,388 B2 | 7/2010 | Pai et al. | |
| 7,776,273 B2 | 8/2010 | Baer et al. | |
| 7,964,350 B1 | 6/2011 | Fekete et al. | |
| 8,288,106 B2 | 10/2012 | Fekete et al. | |
| 8,346,483 B2 | 1/2013 | Kil | |
| 8,715,955 B2 | 5/2014 | Donovan et al. | |
| 8,722,357 B2 | 5/2014 | Baer et al. | |
| 8,828,664 B2 | 9/2014 | Fekete et al. | |
| 9,279,152 B2 | 3/2016 | Fekete et al. | |
| 2001/0038449 A1 | 11/2001 | Baer et al. | |
| 2002/0001837 A1 | 1/2002 | Baer et al. | |
| 2003/0069413 A1 | 4/2003 | Pai et al. | |
| 2005/0239068 A1* | 10/2005 | Bosnes | G01N 33/54306 435/6.18 |
| 2008/0199929 A1* | 8/2008 | Yeung | G01N 1/2813 435/173.1 |
| 2012/0258451 A1* | 10/2012 | Klimanskaya | C12N 5/0621 435/6.1 |
| 2015/0050653 A1 | 2/2015 | Fekete et al. | |
| 2017/0045428 A1 | 2/2017 | Rath et al. | |

OTHER PUBLICATIONS

PCT/US2016/046410, International Search Report and Written Opinion dated Nov. 16, 2016, 1-13.
SIGMA, Biochemical and Reagents for Life Science Research, 2002, 2362.

* cited by examiner

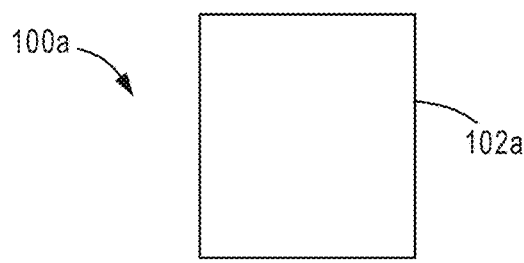
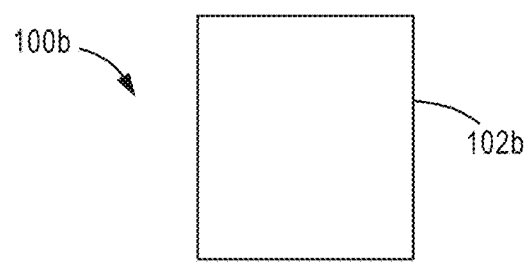
FIG. 1A          FIG. 1B
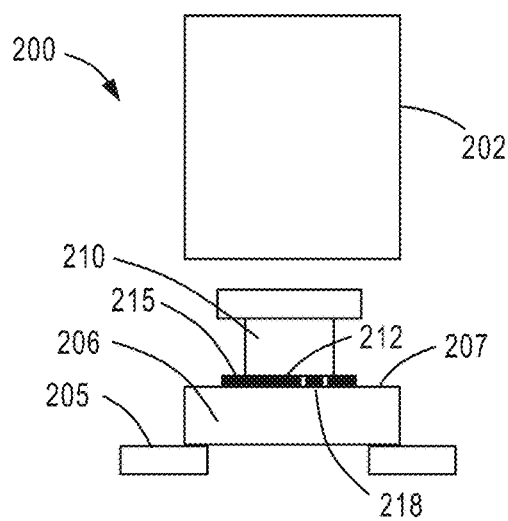
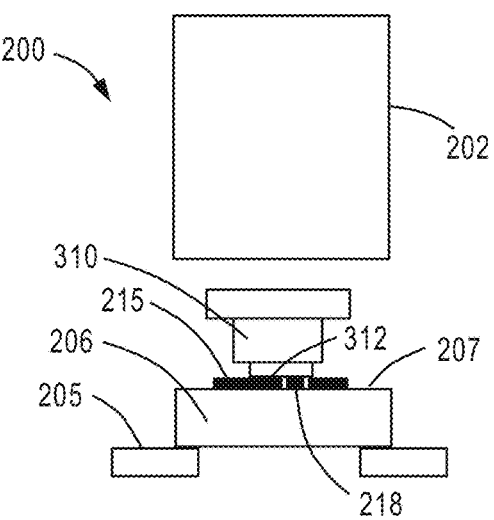
FIG. 2          FIG. 3

Bio Analyzer traces of FFPE Ampliseq Cancer 50 Panel RNA Library:
37°C Overnight (16 hrs) Compared to 65°C 1 hr and 85°C 1 hr Incubation

LCM

MicroCap: 4000 Micron Lung FFPE tissue

1. Place Cap 
2. IR and UV 
3. QC 
4. After

Capture efficiency = 100%

Bio Analyzer traces of FFPE Ampliseq Cancer 50 Panel RNA Library:
37°C Overnight (16 hrs) Compared to 65°C 1 hr and 85°C 1 hr Incubation RNA Yield represented by Ct

| Temp/Time | Mean Ct | Std Error | Lower 95% | Upper 95% |
|---|---|---|---|---|
| 37C/1hr | 32.27 | 0.13 | 32.01 | 32.53 |
| 45C/1hr | 29.18 | 0.13 | 28.92 | 29.44 |
| 55C/1Hr | 29.35 | 0.13 | 29.09 | 29.61 |
| 65C/1hr | 27.57 | 0.07 | 27.42 | 27.72 |
| 75C/1hr | 34.43 | 0.09 | 34.24 | 34.61 |
| 85C/1hr | 38.21 | 0.09 | 38.03 | 38.40 |

Means for Oneway Anova
RNA Yield represented by Ct

| Temp/Time | Mean Ct | Std Error | Lower 95% | Upper 95% |
|---|---|---|---|---|
| 37C/1hr | 36.00 | 0.20 | 35.59 | 36.42 |
| 45C/1hr | 30.97 | 0.20 | 30.55 | 31.38 |
| 55C/1Hr | 30.79 | 0.20 | 30.38 | 31.21 |
| 65C/1hr | 28.90 | 0.12 | 28.66 | 29.14 |
| 75C/1hr | 30.20 | 0.14 | 29.91 | 30.49 |
| 85C/1hr | 34.10 | 0.14 | 33.80 | 34.39 |

BIOLOGICAL SAMPLE PREPARATION FOR TESTING

CROSS-REFERENCE TO RELATED APPLICATIONS

This application claims the benefit of priority of U.S. Provisional Patent Application No. 62/203,311, filed on Aug. 10, 2015, U.S. Provisional Patent Application No. 62/303,227, filed on Mar. 3, 2016, and U.S. Provisional Patent Application No. 62/341,563, filed on May 25, 2016, which applications are incorporated herein in their entirety by reference.

BACKGROUND OF THE INVENTION

Field of the Invention

The present teachings generally relate to compositions, processes, methods, and kits for preparation of samples containing genetic material for downstream detection and/or quantitation analysis.

Description of the Related Art

Laser capture microdissection (LCM) is a technique for selecting or micro dissecting specific cell(s) from a mixed population, usually under microscopic visualization. LCM techniques are used to isolate a single cell or few cells from fresh or archived formalin-fixed paraffin-embedded (FFPE) tissues, blood, semen, or other biological samples. Analysis of nucleic acids extracted using LCM from fresh or archived formalin-fixed paraffin-embedded (FFPE) sections are used to provide information about sample DNA (e.g., genotype) and RNA (e.g., gene expression), for example, as they relate to sample morphology and/or disease state. Using LCM, the biological sample may be examined using a microscope system and individual cells or group of cells may be selected and microdissected using one or more lasers. Through various LCM techniques, the selected sample may be separated from unwanted portions of the larger sample and transferred to a container, such as a well, vial, or tube, for preparing the selected sample for use in a downstream assay, experiment, or test, for instance, in a polymerase chain reaction (PCR) or sequencing assay or workflow.

One objective in many LCM applications is to provide a large yield of quality RNA from fresh or archived FFPE samples. The formalin fixing of an FFPE sample can induce molecular cross-linking within samples, which complicates retrieval of nucleic acids, as well as reduces their yield and quality. This affects the efficiency of downstream detection.

In addition to increasing quality and yield of selected samples from fresh or FFPE specimens, there exists a demand within the field to increase total throughput by reducing the amount of time needed to prepare samples for downstream testing. Existing FFPE RNA Isolation Kits recommend a lengthy overnight Proteinase K (ProK) digestion at 37 degrees Celsius for sample lysis, followed by several purification steps to retrieve RNA from LCM FFPE tissue prior to downstream analysis. This approach also requires sample transfer steps that can introduce additional variability in the yield and quality of the RNA. This multi-step workflow can be especially challenging for RNA isolation from low-input sample types, such as single cells and small populations of rare cells. Consequently, there is a need for an improved LCM FFPE lysis-based solution for extraction of RNA from limited LCM FFPE samples that maintains RNA integrity that increases yield for downstream applications, for example, for PCR or sequencing, such as next generation sequencing (NGS).

Therefore, new methods and systems that aid in the recovery of the high quality RNA from low input LCM-derived FFPE tissue material are highly desirable, as well as improved ways of processing such samples in a manner that reduces processing time and reduces or eliminates transfer of a selected sample.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 1A is a schematic representation of a first system according to embodiments of the present invention.

FIG. 1B is a schematic representation of a second system according to embodiments of the present invention.

FIG. 2 is a schematic representation of a third system according to embodiments of the present invention.

FIG. 3 is a schematic representation of a fourth system according to embodiments of the present invention.

DETAILED DESCRIPTION OF THE DRAWINGS

Figure 4A:
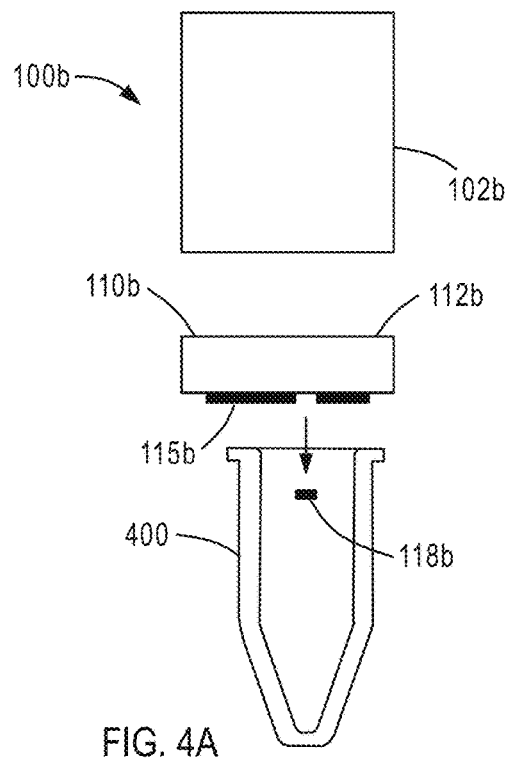
FIGS. 4A and 4B are schematic representations of two methods of processing a selected sample using the system shown in FIG. 1B according to embodiments of the present invention.

As used herein, the term "contact" means in the state or condition of touching or of immediate proximity. Thus, if "A is in contact with B, then A and B are touching or in immediate proximity to one another. Contact between A and B does not necessarily mean that A and B are joined, attached, or bonded to one another, such states are included.

Unless otherwise specified or obvious from its use, the term "about" or "approximately", as used herein, means within ±10% of the stated quantity for which "about" or "approximately" is a modifier.

Referring to FIG. 1A, in certain embodiments of the present invention, a system or instrument 100a is schematically represented. System 100a may be an optical system or instrument, for example, a microscope or a laser capture microdissection (LCM) instrument or apparatus, comprising an optical head 102a. System 100a may further comprise a base 105a configured to receive or support a substrate 110a comprising a surface 112a containing, and/or in contact with, a biological specimen or heterogeneous mixture of biological cells 115a. System 100a may be configured for selecting, separating, isolating, and/or otherwise providing a selected or isolated sample 118a from the biological specimen or heterogeneous mixture of biological cells 115a. Selected sample 118a may comprise a plurality of cells or may comprise a single cell.

Optical head 102a may include one or more lasers configured to remove selected sample 118a from surface 112a and/or to separate or isolate selected sample 118a located on surface 112a. In such embodiments, a laser or other means may be used levitate or otherwise transfer selected sample 118a into a cap, container, tube, capillary, or the like (not shown) for further processing and/or preparation. Selected sample 118a may comprise a fresh sample (e.g., a fresh tissue sample), a formalin-fixed paraffin-embedded (FFPE) sample, or any other type of biological sample (e.g., any biological sample suitable for LCM processing).

Selected sample 118a may be subsequently processed or prepared for a downstream assay, experiment, or test, for example, to detect, quantify, or characterize one or more deoxyribonucleic acid (DNA) molecules or sequences, or to detect, quantify, or characterize one or more ribonucleic acid (RNA) molecules or sequences.

Referring to FIG. 1B, in certain embodiments, a system or instrument 100b is schematically represented. System 100b may be an optical system or instrument, for example, a microscope or a laser capture microdissection (LCM) instrument, comprising an optical head 102b. System 100b may further comprise a base 105b configured to receive or support a substrate 110b comprising a surface 112b containing, and/or in contact with, a biological specimen or heterogeneous mixture of biological cells 115b. System 100b may be configured for selecting, separating, isolating, and/or otherwise providing a selected or isolated sample 118b from the biological specimen or heterogeneous mixture of biological cells 115b. Selected sample 118b may comprise a plurality of cells or may comprise a single cell.

Optical head 102b may include one or more lasers configured to remove selected sample 118b from surface 112b and/or to separate or isolate selected sample 118b located on surface 112b. In such embodiments, gravity or other means, such as a laser, may be used to transfer selected sample 118b into a cap, container, tube, capillary, or the like (not shown) for further processing and/or preparation. Selected sample 118b may comprise a fresh sample (e.g., a fresh tissue sample), a formalin-fixed paraffin-embedded (FFPE) sample, or any other type of biological sample (e.g., any biological sample suitable for LCM processing).

Selected sample 118b may be subsequently processed or prepared for a downstream assay, experiment, or test, for example, to detect, quantify, or characterize one or more DNA molecules or sequences, or to detect, quantify, or characterize one or more RNA molecules or sequences.

Referring to FIG. 4A, a container, receptacle, tube, capillary, or the like may be located below substrate 110b to receive selected sample 118b once it is separated from surface 112b. For example, a container 400 shown in FIG. 4A may be located to receive selected sample 118b as it is transferred via gravity or another external force, such as a force induced by a laser beam. In certain embodiments, a container 410 includes a container cap 412, whereby selected sample 118b may be transfer from substrate 110b to the container cap 412 via gravity or another external force such as, a force induced by a laser beam. Once one or more selected samples 118b have been transferred to container cap 412, the container cap may be inserted into an opening 415 of container 400 so that sample(s) 118b may be received into container 400 and processed further.

Referring to FIG. 2, in certain embodiments, a system or instrument 200 is schematically represented. System 200 may be an optical system or instrument, for example, a microscope or a laser capture microdissection (LCM) instrument, comprising an optical head 202. System 200 may further comprise a base 205 configured to receive or support substrate 206 comprising a surface 207 and a substrate 210 comprising a surface 212 containing. System 200 may be configured for selecting, separating, isolating, and/or otherwise providing a selected or isolated sample 218 from a biological specimen or heterogeneous mixture of biological cells 215. Selected sample 218 may comprise a plurality of cells or may comprise a single cell.

Optical head 202 may include one or more lasers configured to remove selected sample 218 from surface 212 and/or to separate or isolate selected sample 218 located on surface 212. In such embodiments, system 200 and surface 212 of substrate 210 may be configured such that, upon separating substrate 210 from substrate 206, selected sample 218 remains attached and/or in contact with surface 212 and the remaining portions of biological specimen 215 remain attached and/or in contact with surface 207. Selected sample 218 may comprise a fresh sample (e.g., a fresh tissue sample), a formalin-fixed paraffin-embedded (FFPE) sample, or any other type of biological sample (e.g., any biological sample suitable for LCM processing).

In certain embodiments, substrate 210 comprises one or more of a laser capture microdissection cap (LCM cap), sample carrier, or extraction device. Exemplary systems, devices, and methods suitable to select, separate, isolate, and/or otherwise transfer one or more selected sample 218 may be found, but are not limited to, those discussed in U.S. Pat. Nos. 5,859,699 7,075,640, 6,690,470, 8,346,483, 7,456, 938, 8,722,357, 6,528,248, 7,776,273, 7,229,595, 7,749,388, 6,469,779.

During use, each of the surfaces 207, 212 are in contact with the biological specimen 215. System 200 may be configured to select, separate, isolate, and/or otherwise transfer selected sample 218 from surface 207 of substrate 206 to surface 212 of substrate 210. Substrate 210 may be lifted or removed from substrate 206 so that selected sample 218 can be separated from biological specimen 215 for further processing and/or used in an assay, experiment, or test in order to characterize or quantify the content of selected sample 218. For example, selected sample 218 may be subsequently processed or prepared for a downstream assay, experiment, or test, for example, to detect, quantify, or characterize one or more DNA molecules or sequences, or to detect, quantify, or characterize one or more RNA molecules or sequences.

Figure 5A:
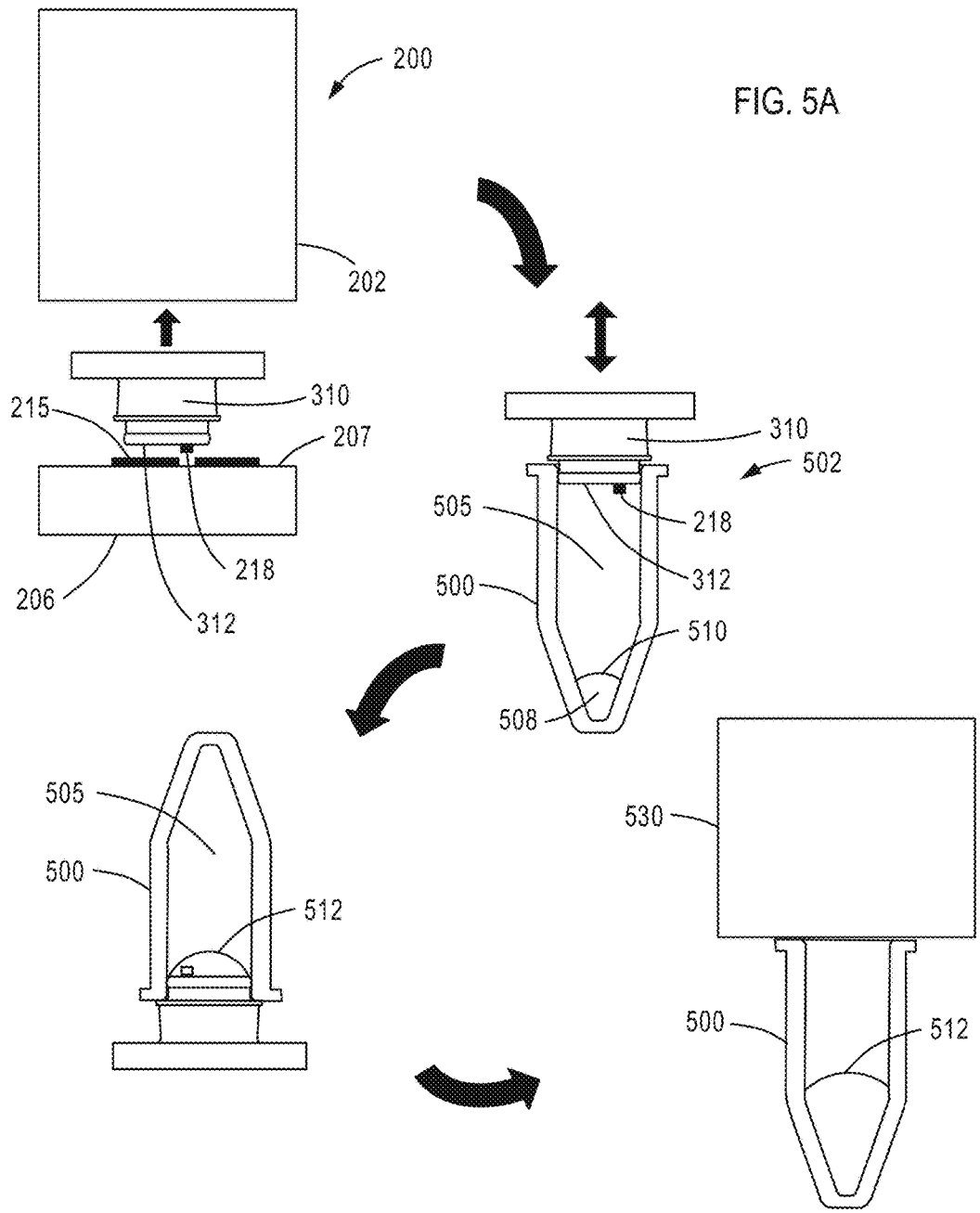
FIGS. 5A and 5B are schematic representations of a method of processing a selected sample using the system shown in FIG. 3 according to an embodiment of the present invention.

Referring to FIG. 3 and FIG. 5A, in certain embodiments, a substrate 310 comprises an LCM cap 310, where surface 312 of LCM cap 310 may have a diameter configured for attachment of LCM cap 310 to a relatively small container 500 (e.g., a container or vial having an internal volume of 0.2 milliliters or about 0.2 milliliters). Embodiments of LCM cap 310 suitable for embodiments of the current invention are discussed in U.S. Provisional Application No. 62/203,311. In certain embodiments, system 200 may be configured for use with both a LCM cap 210 (e.g., for use with containers or vials of a relatively large volume) and LCM cap 310 (e.g., for use with containers or vials of a relatively large volume and vials of a relatively small volume). In such embodiments, LCM cap 210 may be configured to receive a container or vial having a volume of 0.5 milliliters, while LCM cap 310 is configured to receive a container or vial having a volume of 0.5 milliliters or about 0.5 milliliters and a container or vial having a volume of 0.2 milliliters or about 0.2 milliliters.

The use an LCM cap 310 with a container 500 having a volume of 0.2 milliliters or about 0.2 milliliters has been discovered to provide particular advantages in processing certain types of selected samples 218. For example, a 0.2 millimeter container or vial may be used to process selected samples comprising only a few cells or containing only a single cell. As discussed in greater detail below, use of a 0.2 millimeter container or vial may be used in conjunction with LCM cap 310 to advantageously process the selected sample (e.g., by a lysis assay) and, in the same container or vial, perform a downstream assay, experiment, or test. In the context of selected samples (e.g., selected sample 218) comprising only a few cells or a single cell, the use of a single container advantageously helps to preserve the sample solution and reduce contamination that can occur when a sample solution is transferred from contain or vial to another.

Figure 5B:
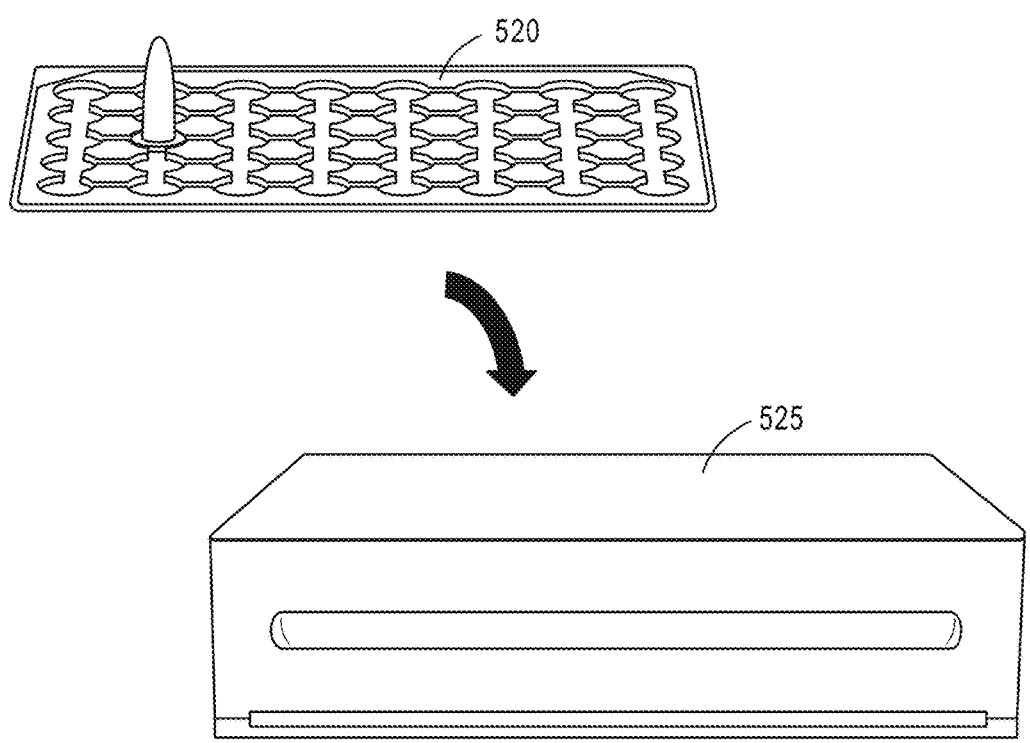

For example, referring to FIG. 5A, in certain embodiments, LCM cap 310 is separated from substrate 206 (top left of FIG. 5A) and moved to a container 500 comprising an internal volume 505 and containing, for example, a volume 508 of a lysis mixture 510. The smaller diameter at surface 212 of LCM cap 310 may subsequently be lowered or fitted onto container 500 (center of FIG. 5A) to provide a closed container 502. In certain embodiments, closed container 502 may be inverted so that lysis mixture 510 contacts selected sample 218 to form a sample solution 512 (bottom left of FIG. 5A). With additional reference to FIG. 5B, LCM cap 310 and container 500 may be placed on a holder, platform, or rack 520. Holder 520, including LCM cap 310 and container 500, may be placed inside an incubator 525 for incubation of selected sample 218. In some embodiments, a plurality of LCM cap 310/container 500 pairs having the same or similar geometry are provided, for example, where each LCM cap 300 contains a respective selected sample 218 provided by system 200 or two or more such systems. In such embodiments, some or all of the LCM caps 310 may be placed on holder 520 and/or be simultaneously placed in incubator 525 for incubation of the selected samples.

In certain embodiments, container 500 comprises a well of a microtiter plate (e.g., of a 96 well microtiter plate or a 384 well microtiter plate) and LCM cap 310 is placed or fitted onto an opening at the top of the well. Additional LCM caps 310, each containing a selected sample 218, may be placed on different ones of the wells of the microtiter plate (e.g., on adjacent wells of the microtiter plate or on wells separated by an intermediate well). Once placed on the microtiter plate, each selected sample 218 may be prepared or processed as discussed further herein (e.g., the selected samples 218 may together be placed in incubator 525, for example, to perform a lysis assay on samples 218).

Additionally or alternatively, other processing of selected sample 218 (alone or with additional samples 218) may be performed within volume as discussed in greater detail below. During processing of selected sample 218 within the volume 505 that is defined by LCM cap 310 and container 500, LCM cap 310 may be removed and re-attached as need (as indicated by the double arrow in center of FIG. 5A) to add other reagents or solutions as prescribed or needed. Once preparation and processing of sample 218 is completed, LCM cap 310 may be removed, and sample 218 may be placed into or attached to an instrument 520 for performing a downstream assay, experiment, or test on sample solution 512, which now contains the processed version of the initially selected sample 218. Advantageously, the entire process, from obtaining the selected sample 218 to performing an assay, experiment, or test on the processed sample solution 512, takes place with selected sample 218 confined to surface 312 of LCM cap 310 and/or volume 505 of container 500.

Figure 4B:
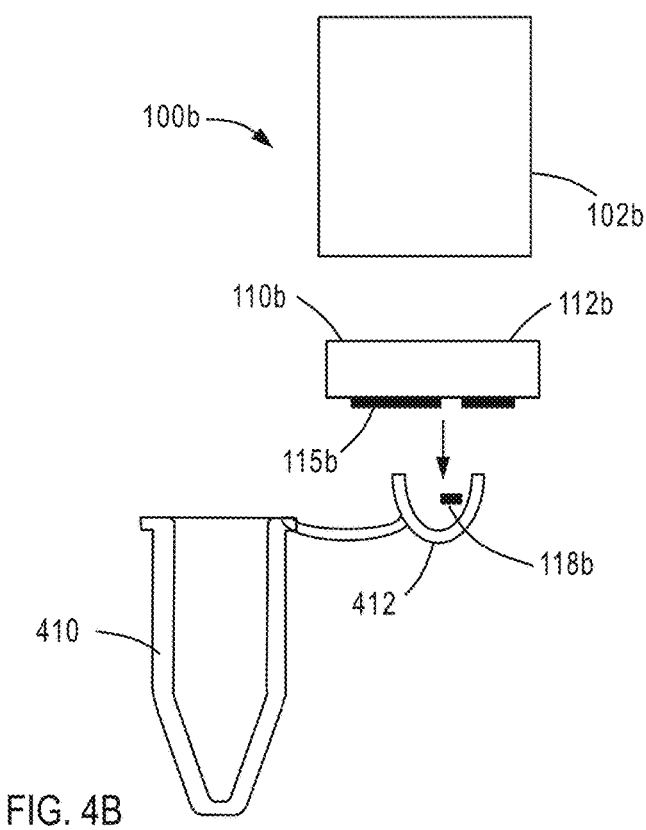

The above example of processing and preparing a selected was primarily with reference to system 200 and LCM cap 310 substrate. However, it will be appreciated that at least portions of the previous paragraphs may be applied to systems 100a, 100b and to substrates 110a, 110b, and 210 for preparing selected samples such as selected samples 118a or 118b. For example, a selected sample (e.g., selected sample 118a or 118b, or selected sample 218 selected using substrate 210) and a lysis mixture may be brought into contact with one another when (e.g., as discussed above in reference to FIGS. 1, 4A, and 4B) a selected sample is lowered, falls, or is levitated into a container.

In the previous embodiment using LCM cap 310 or in embodiments based on use of substrates 110a, 110b, or 210, a lysis mixture may be added to the container (e.g., container 400, 500 and/or container cap 412) when the selected sample is so collect. Alternatively, the lysis mixture may be added to the container prior to collection of the selected sample. The lysis mixture may comprise a buffer system configured to provide a direct lysate to qPCR workflow. Additionally or alternatively, the lysis mixture may comprise a buffer system configured to provide a direct lysate to sequencing assay workflow.

Figure 6:
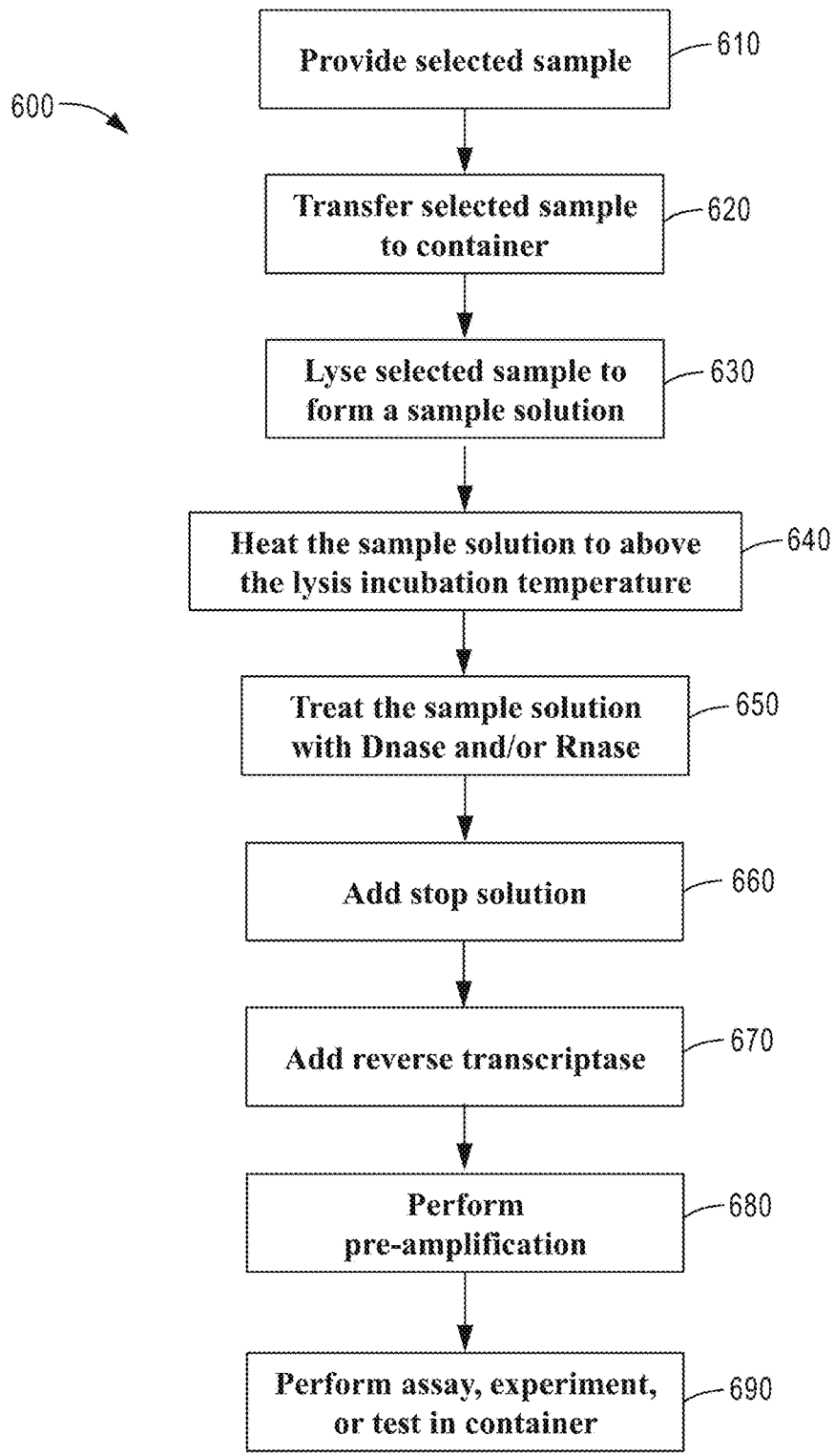
FIG. 6 is a schematic representation of a method for processing a selected sample according to embodiments of the present invention.

Referring to FIG. 6, in certain embodiments, a method 600 for processing a selected sample (e.g., selected samples 118a, 118b, or 218) containing (e.g., in container 400, 500) one or more nucleic acids includes an element 610, which comprises providing a selected sample comprising one or more biological cells. Method 600 further includes an element 620, comprising placing, locating, or transferring the selected sample into an internal volume of a container (e.g., as discussed above in relation to selected samples 118a, 118b, or 218 into, for example, internal volume 505 of container 500 or the internal volume of container 400).

Method 600 also includes element 630, comprising contacting the selected sample with a lysis mixture (e.g., lysis mixture 510) using a protocol to form or provide a sample solution (e.g., the sample solution 512 formed by selected sample 218 and lysis mixture 510) within the internal volume of the container. The protocol may include reagents and procedures for lysing the selected sample. As discussed below, the protocol may also include other reagents and procedures for processing and preparing the selected sample for downstream assays, experiments, or tests. The lysis mixture may comprise one or more of:

A low ionic strength detergent-based buffer system.

A Proteinase K.

A lysis mixture has a volume that is less than or equal to 10 microliters.

Exemplary formulation for lysis mixtures include, but are not limited to, those discussed in U.S. Pat. No. 7,964,350. Embodiments in which the lysis mixture volume is 10 microliter or less have been found to be useful where the selected sample contains only one or a few cell and/or in combination with an container (e.g., container 400 or 500) have a volume of about 0.2 milliliters or less. In such embodiments, a great benefit has been discovered doing all processing in a single container.

In certain embodiments, the protocol according to method 600 comprises heating the sample solution (e.g., sample solution 512) to a first temperature that is greater than 37 degrees Celsius and less than or equal to 75 degrees Celsius. As discovered during experiments discussed below and shown in FIGS. 9, 10, 12, and 14-18, lysis assays conducted at a temperature above 37 degrees Celsius were found to increase yield of a target DNA or RNA from a selected sample. This was demonstrated experimentally by a lower Ct value (e.g., average number of thermal cycles in a qPCR amplification process) for assays conducted at temperatures above 37 degrees Celsius as compared to the Ct values of assays conducted at 37 degrees Celsius. In certain embodiment, it was discovered that the yield for both DNA and RNA was higher at lysis assay temperature of 65 degrees Celsius or at about 65 degrees Celsius (e.g., 65 degrees Celsius ±1 degrees Celsius) than at temperatures below or above this temperature condition. In certain sets of lysis protocols conducted, a lysis temperature greater than or equal to 45 degrees Celsius, or 55 degrees Celsius, and less than or equal to 75 degrees Celsius was found produce a better DNA and/or RNA yield than when the lysis assay was conducted either above or below these temperature conditions.

In certain embodiments, the protocol of element 630 of method 600 comprises a first incubation for assaying the selected sample that is performed over a first incubation period and at the first temperature (e.g., at a temperature of about 65 degrees Celsius). The first incubation period is less than or equal to 2 hours or less than or equal to 1 hour. Experiment according to embodiments of the present invention as discussed below were generally conducted over an incubation period of about 1 hour and provided the advantage of increased DNA and RNA yields. Lower incubation periods advantageously allow more target samples to be processed over a given period of time.

In certain embodiments, the protocol according to method 600 may include an element 640, comprising exposing the sample solution (e.g., sample solution 512) to second temperature that is greater than the first temperature, for example, at a temperature of at least 85 degrees Celsius. Element 640 may further comprise a second incubation at the elevated temperature that follows the first incubation, wherein the second incubation period is at least 15 minutes or about 15 minutes (e.g., 15 minutes, 30 minutes, 45 minutes, or 60 minutes). The duration of the second incubation may be selected to balance demands of increase yield and higher processing throughput for a particular application. In certain embodiments, the second incubation at the higher temperature may be used to decreases a molecular crosslinking of nucleic acid molecules within the sample solution.

In some embodiments, method 600 additionally includes an element 650, comprising adding a deoxyribonuclease (DNase) and/or a ribonuclease (RNase) to the sample solution (e.g., sample solution 512), which may result in a modified or larger sample solution (e.g., sample solution 512). In some embodiments, the temperature of the solution is lowered from the first temperature (used during lysing), either before or after addition of the DNase and/or RNase. For example, the solution temperature may be lower to a temperature below 40 degrees Celsius (e.g., to a temperature the is at 37 degrees Celsius or is about 37 degrees Celsius or a temperature that is below 37 degrees Celsius, for example, to room temperature). In certain embodiments, the sample solution comprises both a DNA molecule and an RNA molecule and different portions of the solution are treated with either RNase or DNase. In such embodiments, the solution within the container (e.g., container 400 or container 500) may be divided to provide a first portion of the sample solution remaining the container and portion transferred (e.g., poured or pipetted) to a second container. An RNase reagent may be added to either the first portion or the second portion, wherein DNA assay, experiment, or test may be performed on that portion. A DNase reagent may be added to the other portion so that an RNA assay, experiment, or test may be performed on that portion. In certain embodiments, the at least a portion of the first and/or second portions may be transferred to a third container for the same sample preparation and/or downstream assay, test, or experiment as the first or second portions. Alternatively, the third portion may be processed differently than the first or second portions and/or be included in a different downstream assay, test, or experiment than either the first or second portions.

In certain embodiments, method 600 may further include an element 660, comprising adding a stop solution to the sample solution (e.g., sample solution 512). In the case of RNA samples, method 600 may also include an element 670 comprising adding a reverse transcriptase to the sample solution (e.g., for converting RNA molecules to cDNA molecules). Method 600 may additionally include an element 670, comprising performing a preamplification assay on the sample solution prior to performing the assay, experiment, or test on the sample solution. In some embodiments (e.g., where there is only small amount or number of a particular type of molecule, such as a RNA or DNA target molecule), method 600 may include an element 680, comprising performing a preamplification assay on the sample solution prior to performing an assay, experiment, or test on the sample solution for detection, analysis, quantification of one or more molecules from the separated sample. Examples of solutions and assays for processing the selected sample include, but are not limited to, those discussed in U.S. Pat. No. 7,964,350.

In various embodiments, method 600 may include an element 690, comprising performing one or more assays, experiments, or tests in the same container (e.g., container 400 or 500) used to initially lyse the selected sample (e.g., selected sample 118a, 118b, or 218). The assay, experiment, or test may include one or more of:

A polymerase chain reaction (PCR) assay, experiment, or test.

A quantitative PCR (qPCR) assay, experiment, or test.

A digital PCR assay, experiment, or test.

A genotyping assay, experiment, or test.

A sequencing assay, experiment, or test.

The sequencing assay, experiment, or test may comprise capillary electrophoresis assay, experiment, or test or next generation sequencing assay, experiment, or test. The next generation sequencing assay, experiment, or test comprises one or more of:

A single-molecule sequencing assay, experiment, or test.
An Ion semiconductor assay, experiment, or test.
A pyrosequencing assay, experiment, or test.
A sequencing by synthesis assay, experiment, or test.
A sequencing by ligation assay, experiment, or test.
A chain termination assay, experiment, or test.
A Sanger sequencing assay, experiment, or test.

In certain embodiments, a sample solution may comprise a first population of a first molecule and a second population of a rare molecule, wherein the second population is less than the first population. In such embodiments, the assay, experiment, or test comprises an assay, experiment, or test for detecting, analyzing, or quantifying the rare molecule.

One or more of the above elements of method 600 may be omitted or modified. For example, element 670 (adding a reverse transcriptase) may be omitted if a DNA assay, experiment, or test are to be conducted on the sample solution. In other embodiments, element 640 (processing at a temperature above the nominal lysing temperature) may be omitted. In yet other embodiment element 690 may be omitted and all or a portion of the sample solution may be transferred to a different container for a downstream assay, experiment, or test.

EXAMPLES

Support for at least some of claimed and/or disclosed embodiments of the current invention are supported by various experiments and tests discussed below and found in FIGS. 7-18.

Disclosed workflows disclosed and/or experimentally tested combine three components that may be used in various combinations to allow or provide efficient lysis and/or extraction of RNA from LCM captured fresh and/or FFPE tissue/cell lysate:

1) LCM cap was configured to be attached to low volume containers (e.g., container have a volume of about 0.2 milliliters or less) (see U.S. Provisional Application No. 62/203,311 for suitable embodiments of an LCM cap).

Figure 7:
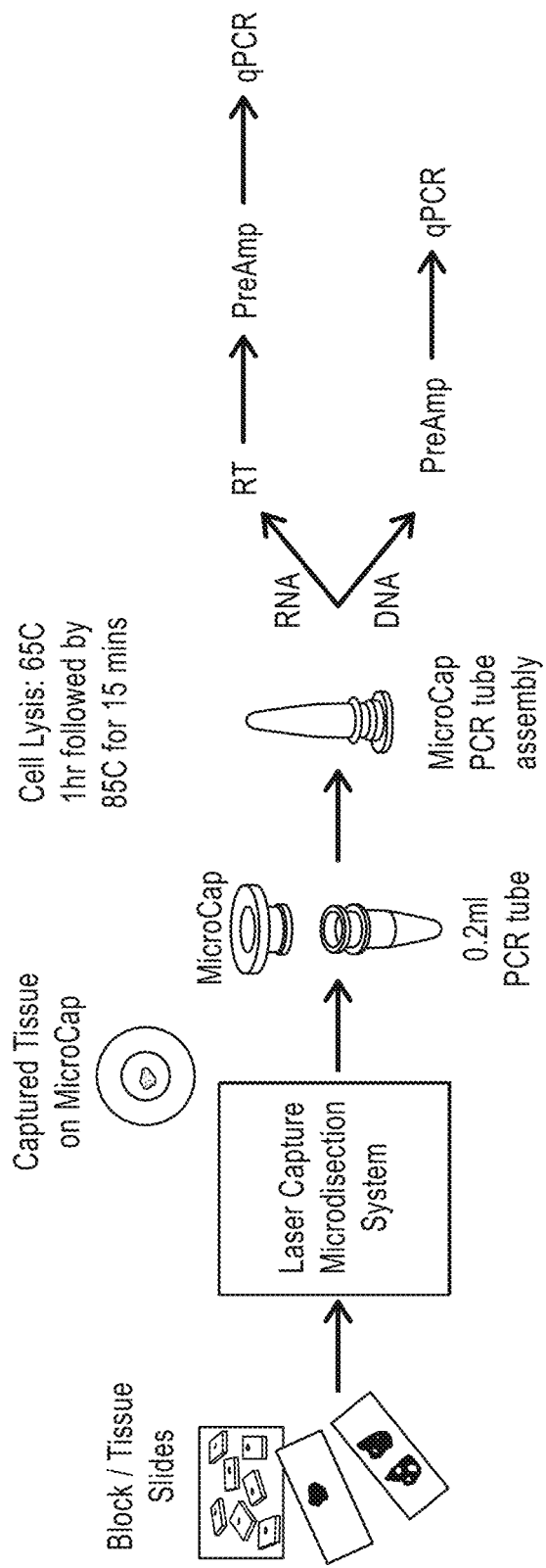
FIG. 7 is a schematic representation of workflows according to embodiments of the current invention.

2) Buffer formulations for direct FFPE lysis in a small volume (e.g., about 0.2 milliliter container volume and/or a lysis mixture volume that is less than or equal to 10 microliters or about 10 microliters), 3) Predetermined lysis conditions for FFPE (incubation temperature and time) (e.g., FIG. 7).

Figure 8:
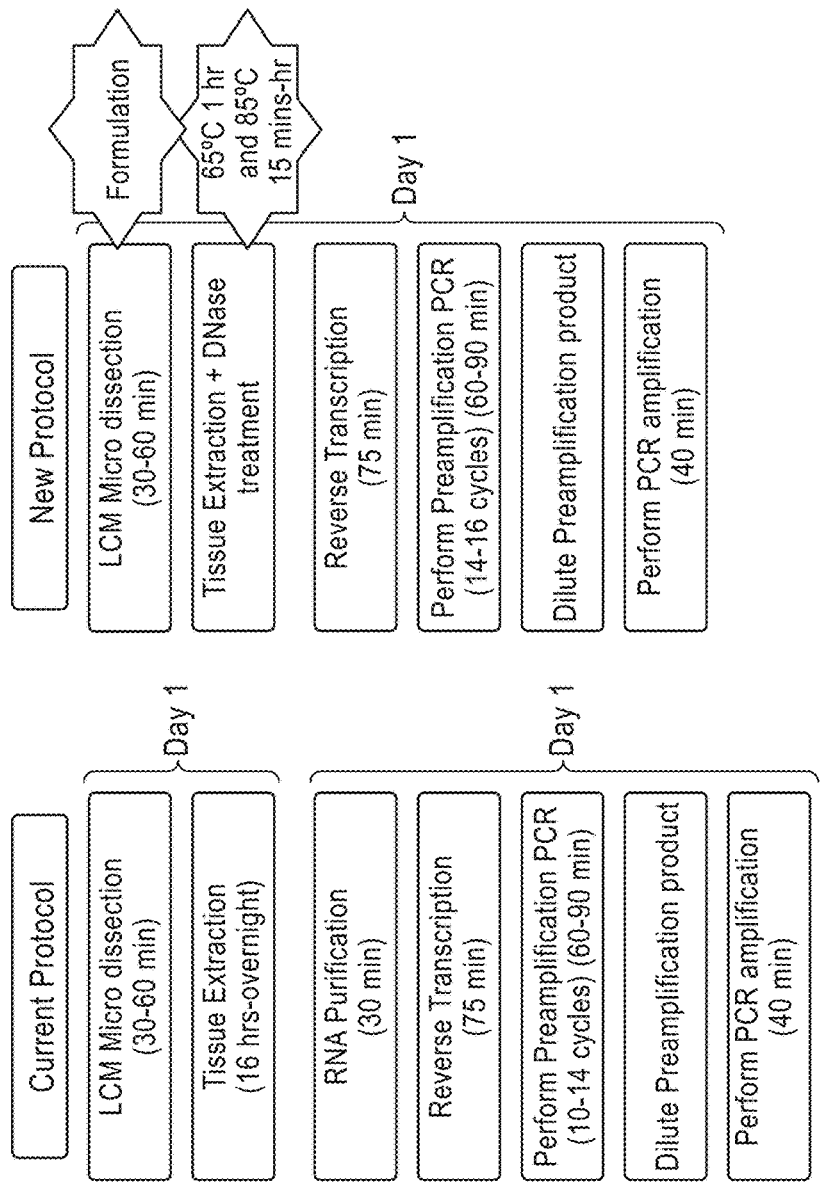
FIG. 8 is a schematic representation of a prior art LCM to PCR protocol workflow ("Current Protocol") and of an LCM to PCR protocol workflow according to an embodiment of the current invention ("New protocol").

Together, these components enable an extraction workflow to be completed in a single collection tube. Moreover, these elements are compatible with a single-tube qPCR workflow (FIG. 8).

Figure 9:
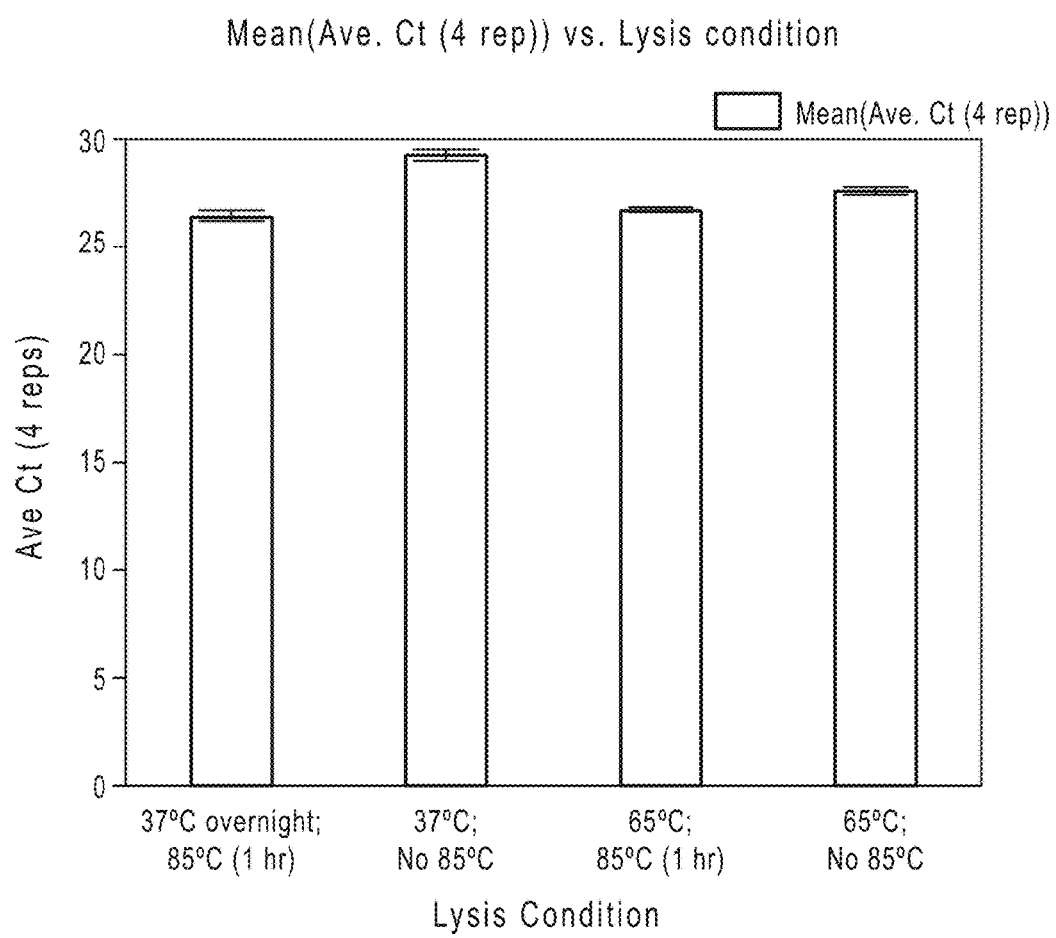
FIG. 9 is a bar graph showing RNA yield in terms of average Ct value for various lysis conditions or protocols.

For example FIG. 9 shows results for an LCM cap used in combination with a small volume container (0.2 milliliter) using LCM FFPE isolated RNA qPCR performance with Specific NSCLC targets (Lung Cancer FFPE tissue block >1 year old).

The LCM cap compatible with a 0.2 ml PCR container was used to process LCM FFPE cell/tissue isolates—from sample collection through detection—in a single tube, which minimizes sample losses associated with multi-tube workflows (for example, a LCM cap compatible with a 0.2 milliliter container). In addition, the flexibility to use a small lysis volume (10 microliter) enables our customers to increase sample concentration as well sensitivity for downstream workflows, which is especially beneficial when working with very small LCM samples such as single cells. Our lysis based solution workflow leverages the Cells to Ct buffer formulation, which is a low ionic strength detergent-based buffer system suitable for direct lysate to qPCR workflow. Many literatures have sited that the yield and recovery of RNA gets better with higher temperature and short incubation. In this proposed workflow the cell lysis condition was achieved by heating the micro-dissected LCM FFPE cells or tissue lysate at 65 degrees Celsius for <1 hour instead of 37 degrees Celsius overnight (16 hours). Additional advantage of lysing the LCM micro dissected cells at 65 degrees Celsius is to enable multi-analyte unified workflow to extract DNA and RNA from same LCM tissue lysate. Alternatively, the proposed workflow can be used to isolate RNA and genomic DNA alone from LCM FFPE tissue lysate. Increasing the temperature of cell lysis condition from 37 degrees Celsius to 65 degrees Celsius has shown improvements in RNA yield (FIG. 9). Since FFPE samples have substantial RNA crosslinking that could affect the efficiency of the RT enzyme, we recommend heating the sample for 15 mins at 85 degrees Celsius after cell lysis step to improve molecular de-crosslinking. Incubation time optimization study with the 85 degrees Celsius step (15 minutes, 30 minutes, and 1 hour) indicated no statistical significant difference between samples.

Figure 10:
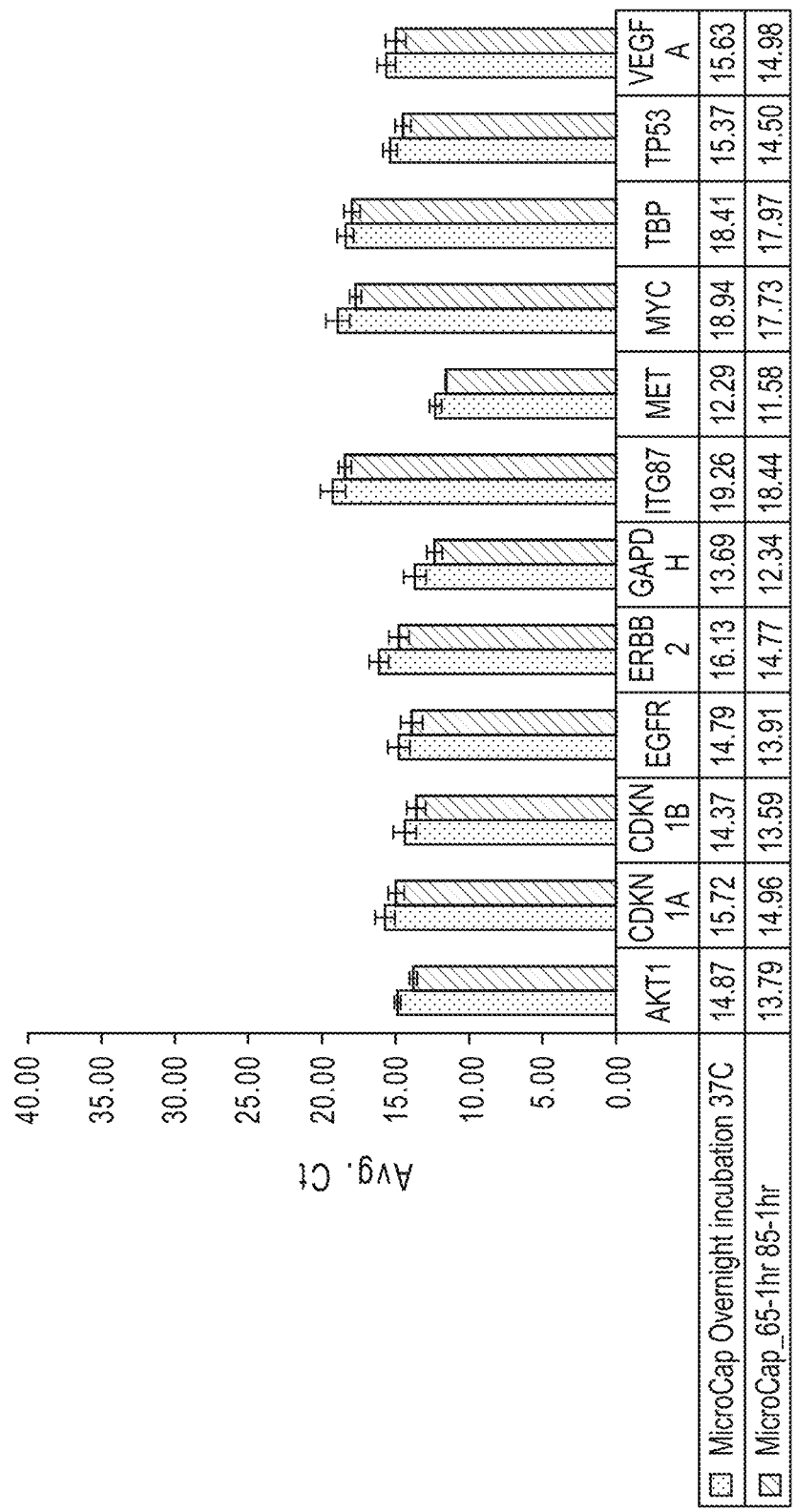
FIG. 10 is a bar graph showing LCM FFPE isolated RNA qPCR performance with Breast cancer FFPE tissue block >2 years old according based on two different lysis conditions or protocols.

Referring to FIG. 9, LCM tissue slides were prepared from Lung (NSCLC) block >1 year old and Breast cancer FFPE block >2 year old. Preliminary workflow feasibility was achieved by performing RT-qPCR with cancer specific assays tested with RNA obtained from LCM tissue lysate incubated at 37 degrees Celsius overnight and our improved LCM FFPE tissue RNA extraction protocol (65 degrees Celsius 1 hour and 85 degrees Celsius 15 mins-1 hr). Proposed LCM FFPE cell extraction workflow (65 degrees Celsius 1 hr and 85 degrees Celsius 15 mins—1 hr) indicated better/comparable performance with respect to existing (37 degrees Celsius—overnight) protocol for majority of assays (control and target) tested in this study (FIG. 9 and FIG. 10). The improved workflow according to an embodiment of the present invention took advantage of an LCM cap compatible with a 0.2 milliliter container, offering low volume flexibility, and providing compatibility with a single-tube qPCR workflow. Feasibility data with improved cell extraction protocol indicated successful extraction of qPCR and NGS grade RNA from micro-dissected LCM-FFPE cells or tissue with a shorter turnaround time (>80%) compared to current (37 degrees Celsius—overnight) cell extraction protocol, which is highly desirable for modern genomic analysis.

Referring to FIG. 10, a study was performed using FFPE 7 micron section from a year old NSCLC FFPE block and qPCR analysis was performed on RNA samples processed from a 200-micron FFPE region micro dissected using LCM cap compatible with a 0.2 ml PCR tube. Optimized FFPE—RNA 2 hours lysis protocols indicated comparable result compared to current 37 degrees Celsius O/N (16 hours) incubation. All control and targeted assays tested for NSCLC lung carcinoma are detected with both our current FFPE RNA extraction method as well as the improved one. Each bar represents duplicate sample preparations and quadruple PCR replicates.

Figure 11:
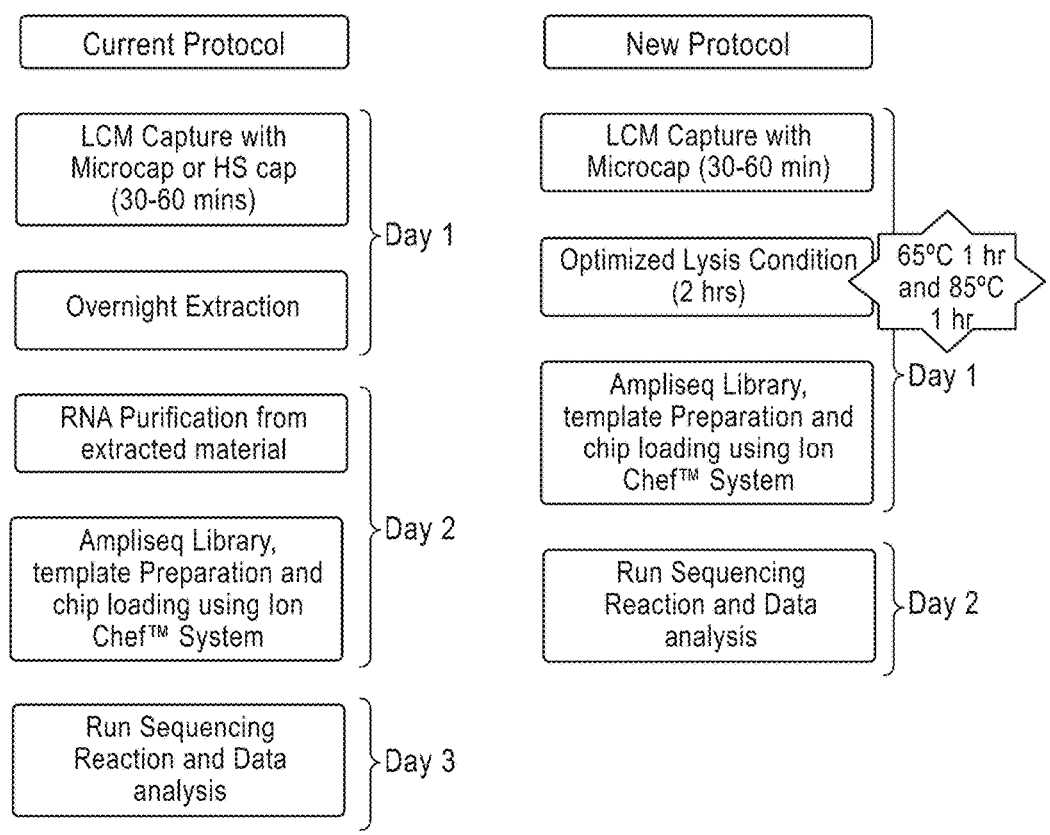
FIG. 11 is a schematic representation of a prior art LCM to sequencing protocol ("Current Protocol") and of an LCM to sequencing protocol workflow according to an embodiment of the current invention ("New protocol").
Figure 12:
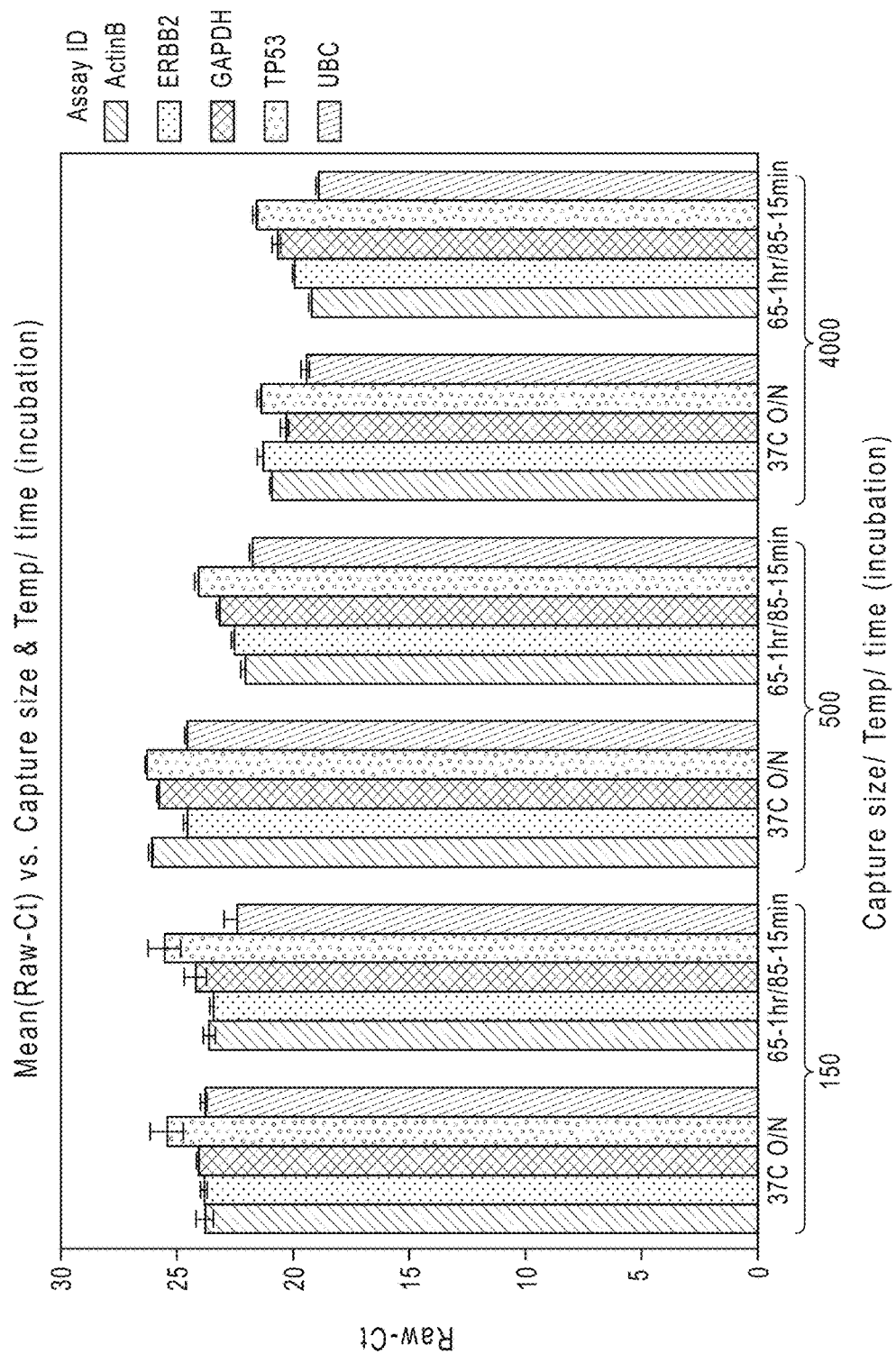
FIG. 12 is a bar graph showing RNA yield in terms of average Ct value for various lysis conditions according to the 1-day LCM to PCR protocol workflow shown in FIG. 8.
Figure 13A:
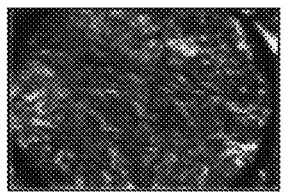
FIG. 13 is an illustrative summary of a NGS RNA yield and Library data with an Ampliseq Cancer 50 Panel.
Figure 13A:
Figure 13A:
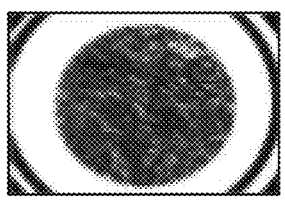
Figure 13A:
Figure 13A:
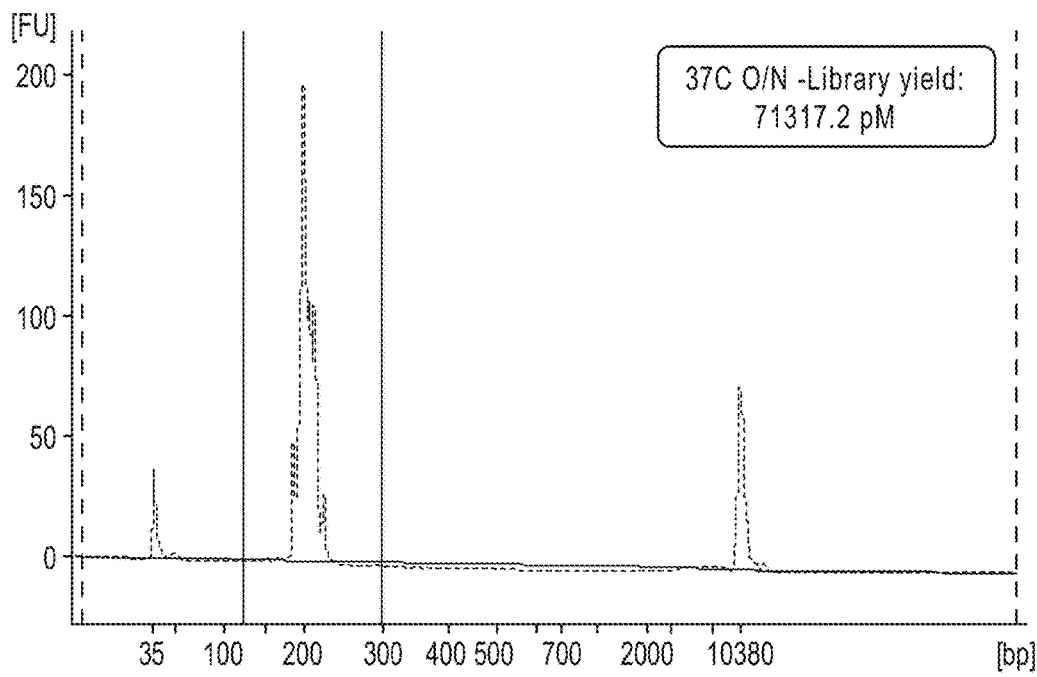
Figure 13B:
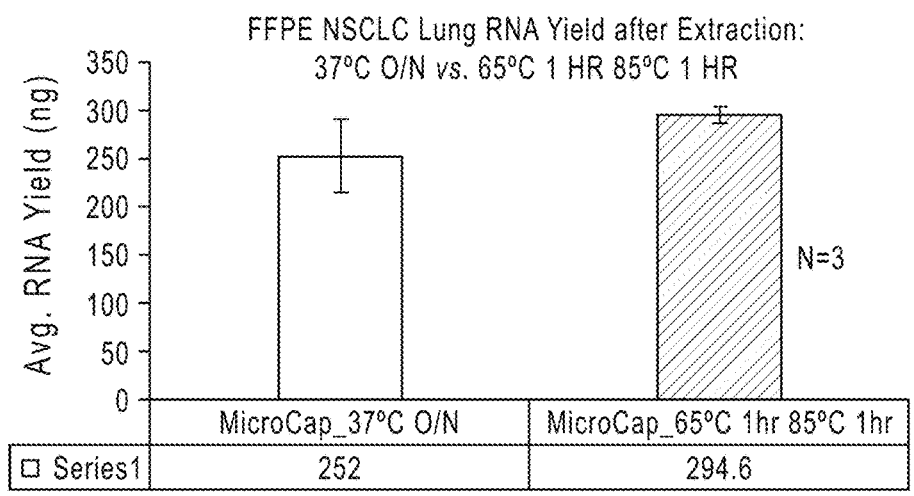
Figure 13B:
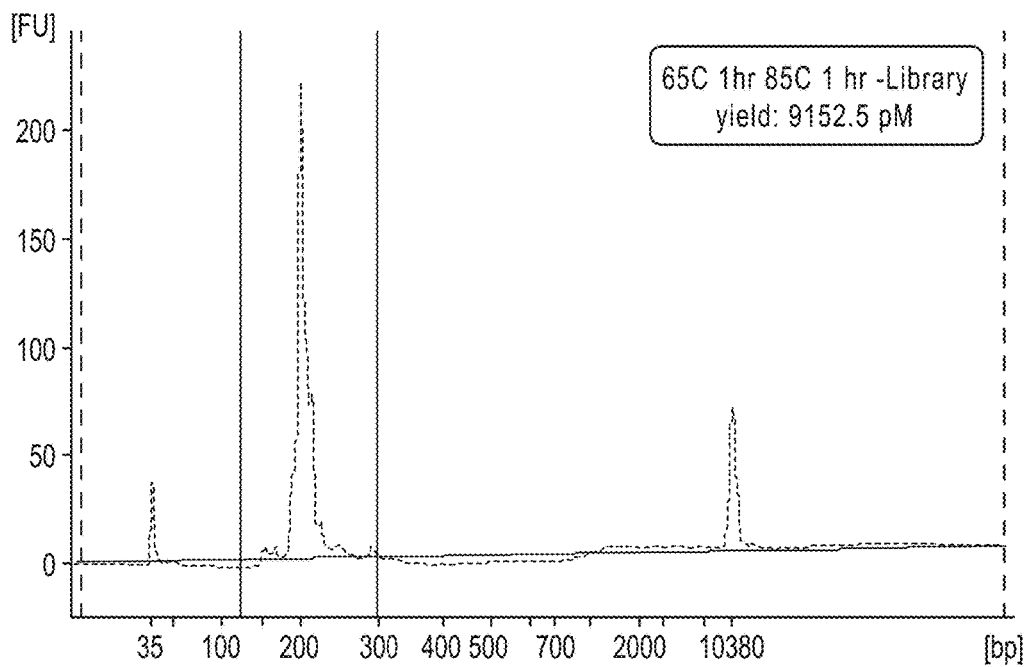

Referring to FIGS. 11 and 12, a study was performed using FFPE 7 micron section from a >2 year old Breast FFPE block and qPCR analysis was performed on RNA samples processed from a 150, 500 and 4000-micron FFPE region micro dissected using an LCM cap compatible with a 0.2 ml PCR tube. Optimized FFPE—RNA<than 2 hours lysis protocols indicated comparable/better result with respect to current 37 degrees Celsius overnight (16 hours) incubation. Each bar represents triplicate sample preparations and quadruple PCR replicates.

Figure 14:
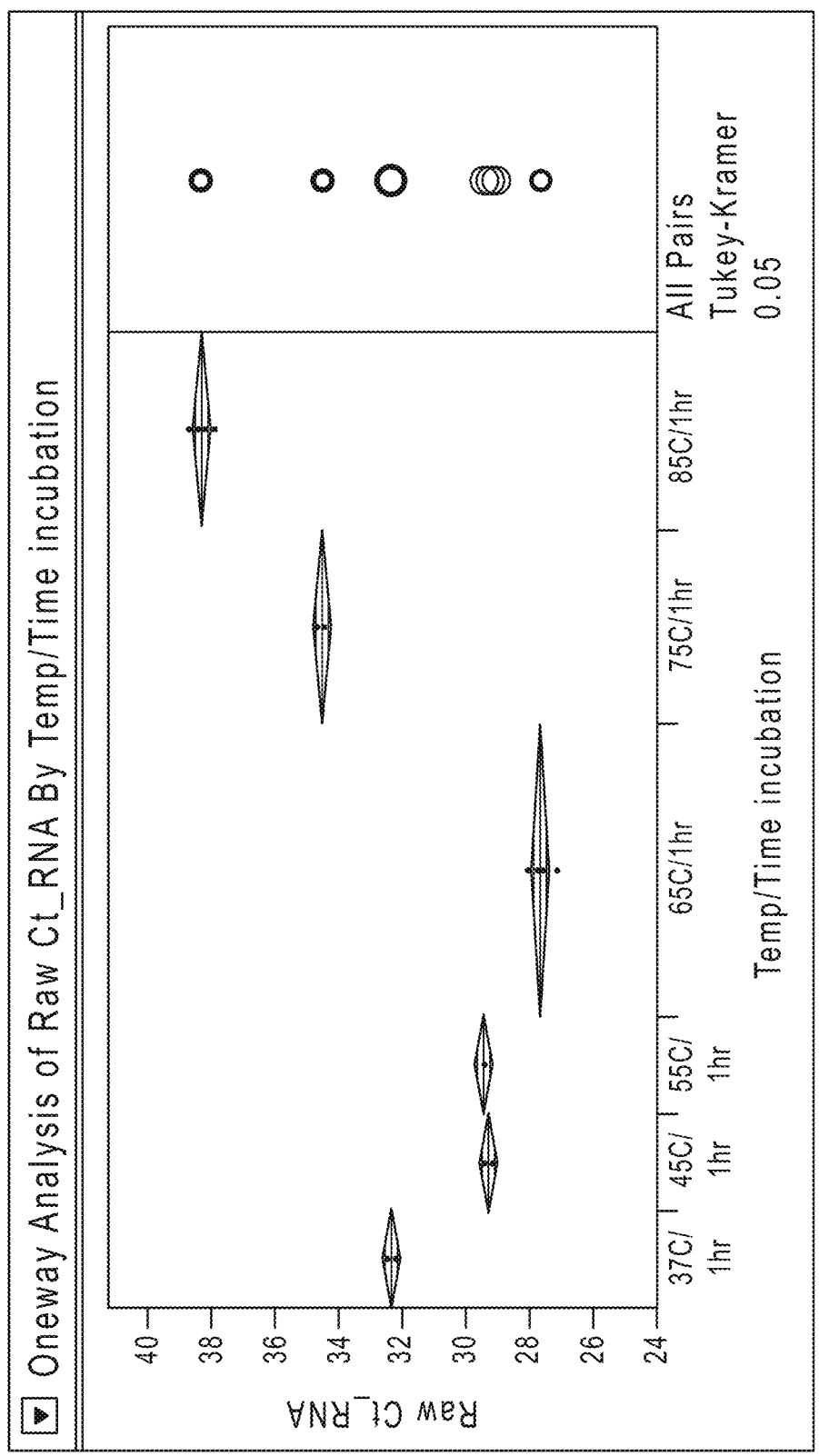
FIGS. 14-16 are results from experiments for an RNA sample, useful to demonstrate advantages of embodiments of the present invention.
Figures 15, 16:
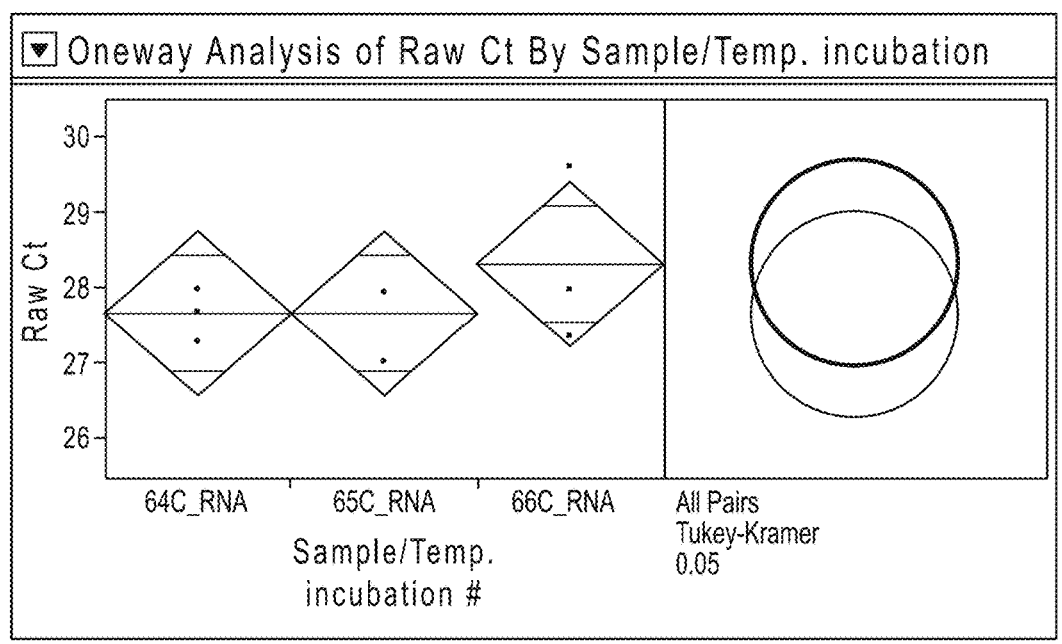
Figures 17, 18:
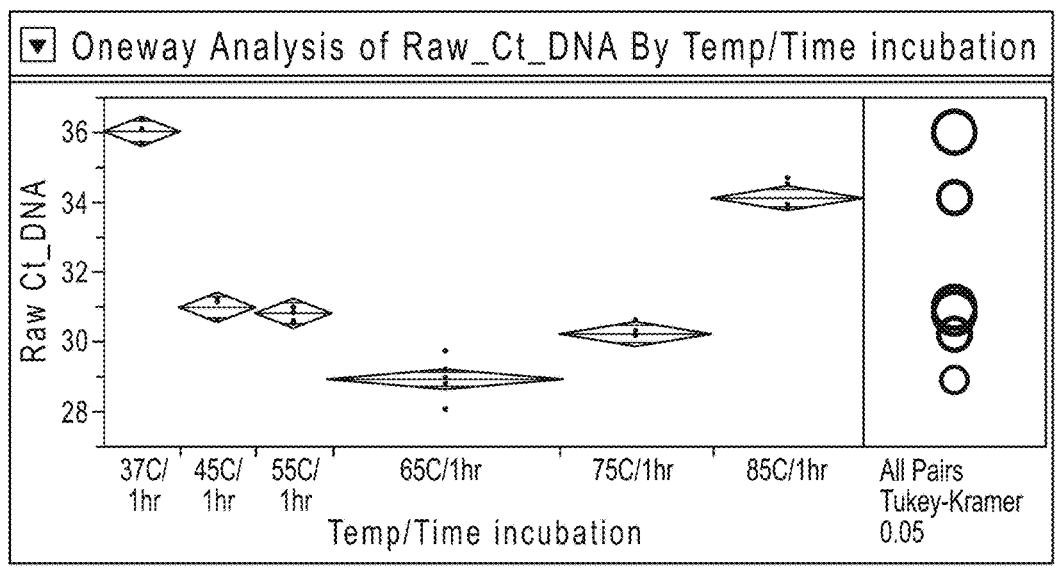
FIGS. 17-19 are results from experiments for a DNA sample, useful to demonstrate advantages of embodiments of the present invention.
Figure 19:
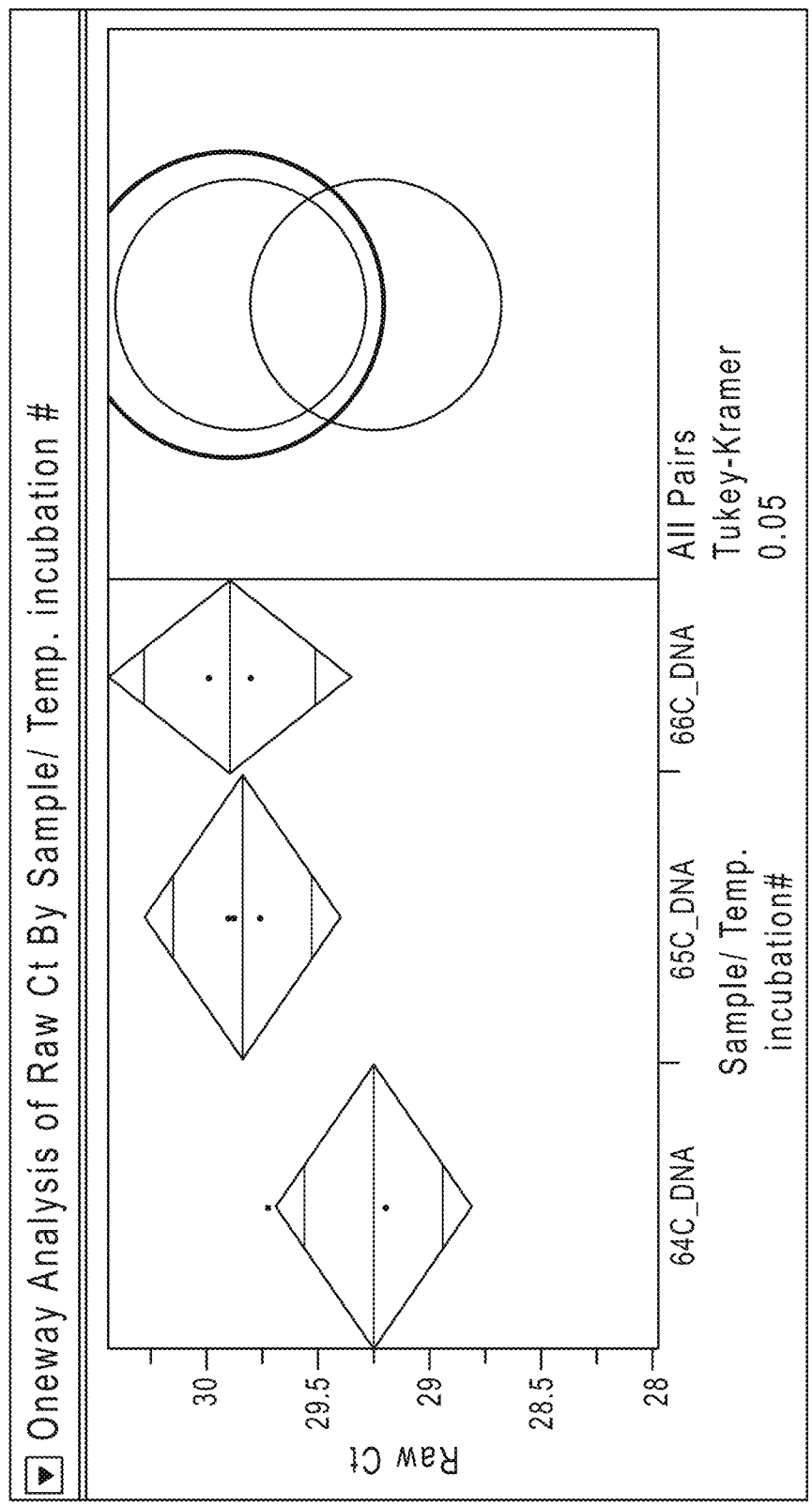
Figure 20:
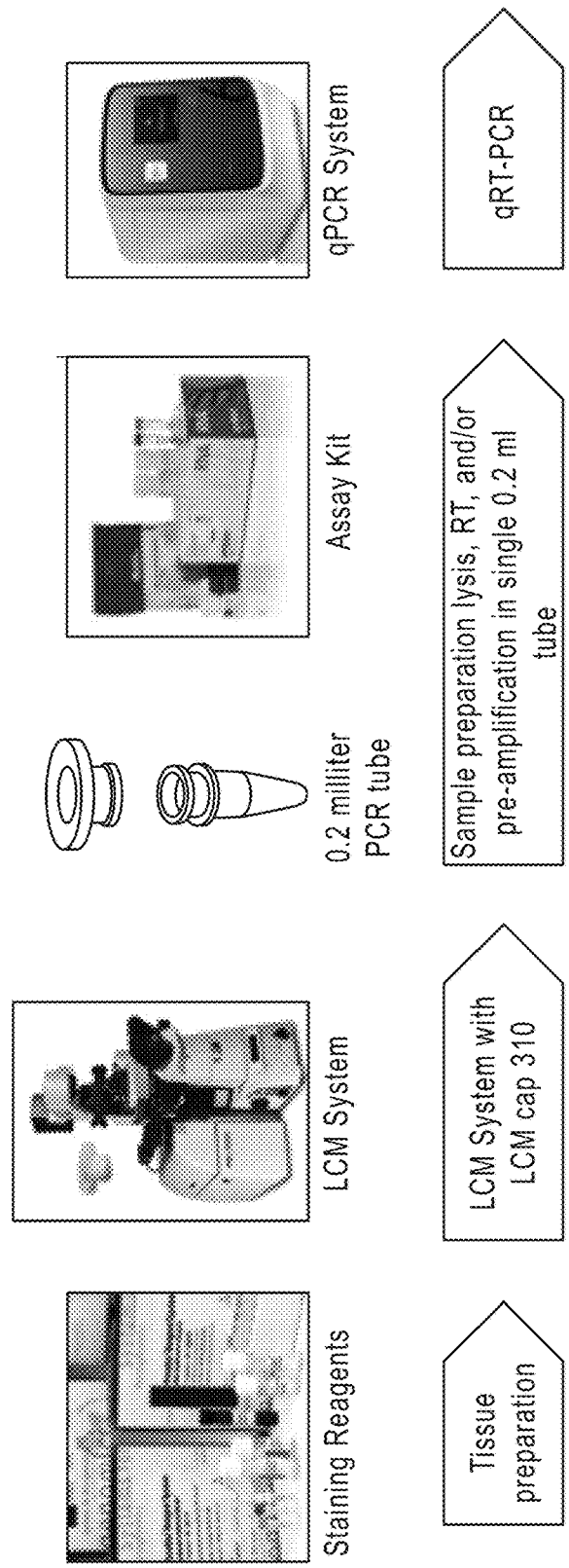
FIG. 20 is an illustrative summary of a method according to an embodiment of the current invention.
Figure 21:
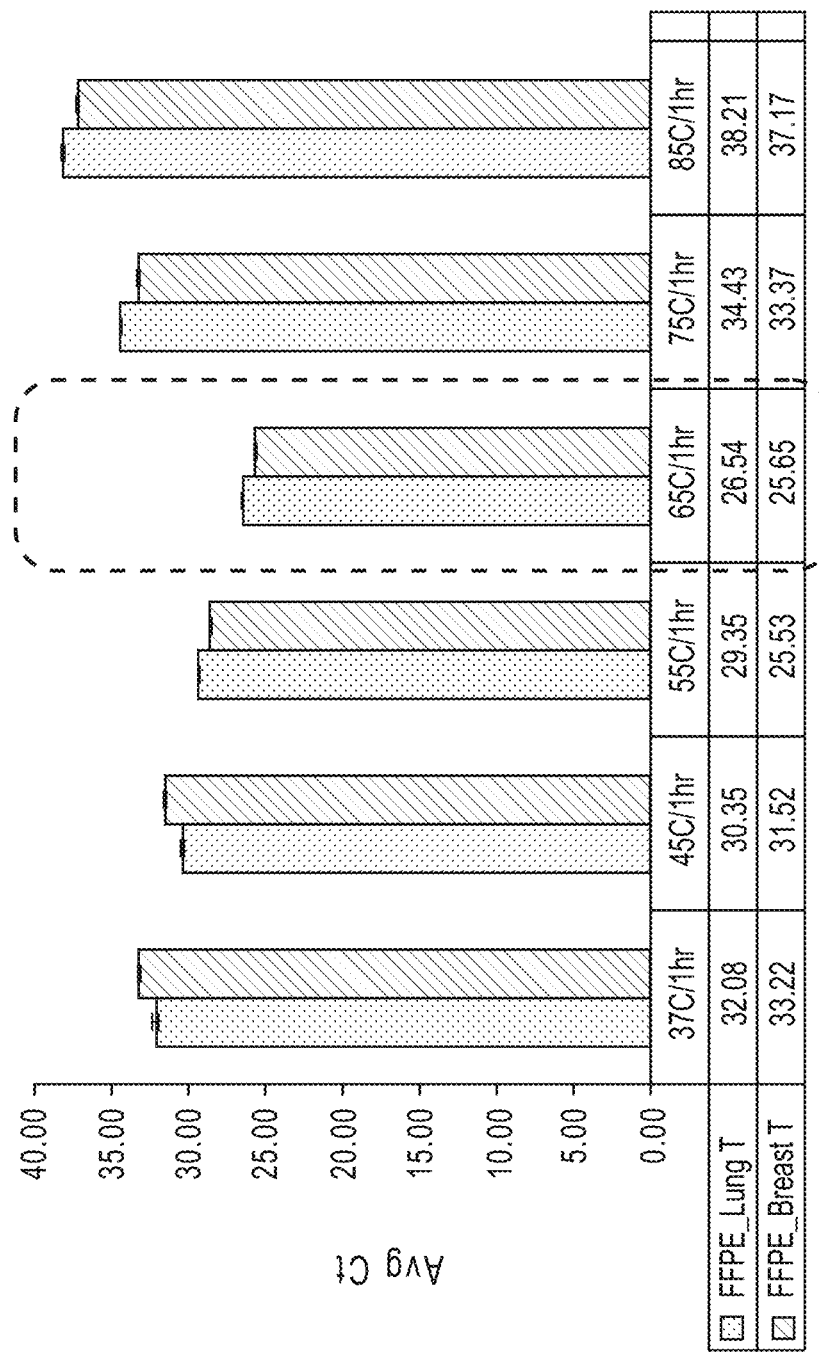
FIGS. 21-24 are result from experiments useful to demonstrate advantages of embodiments of the present invention
Figure 22:
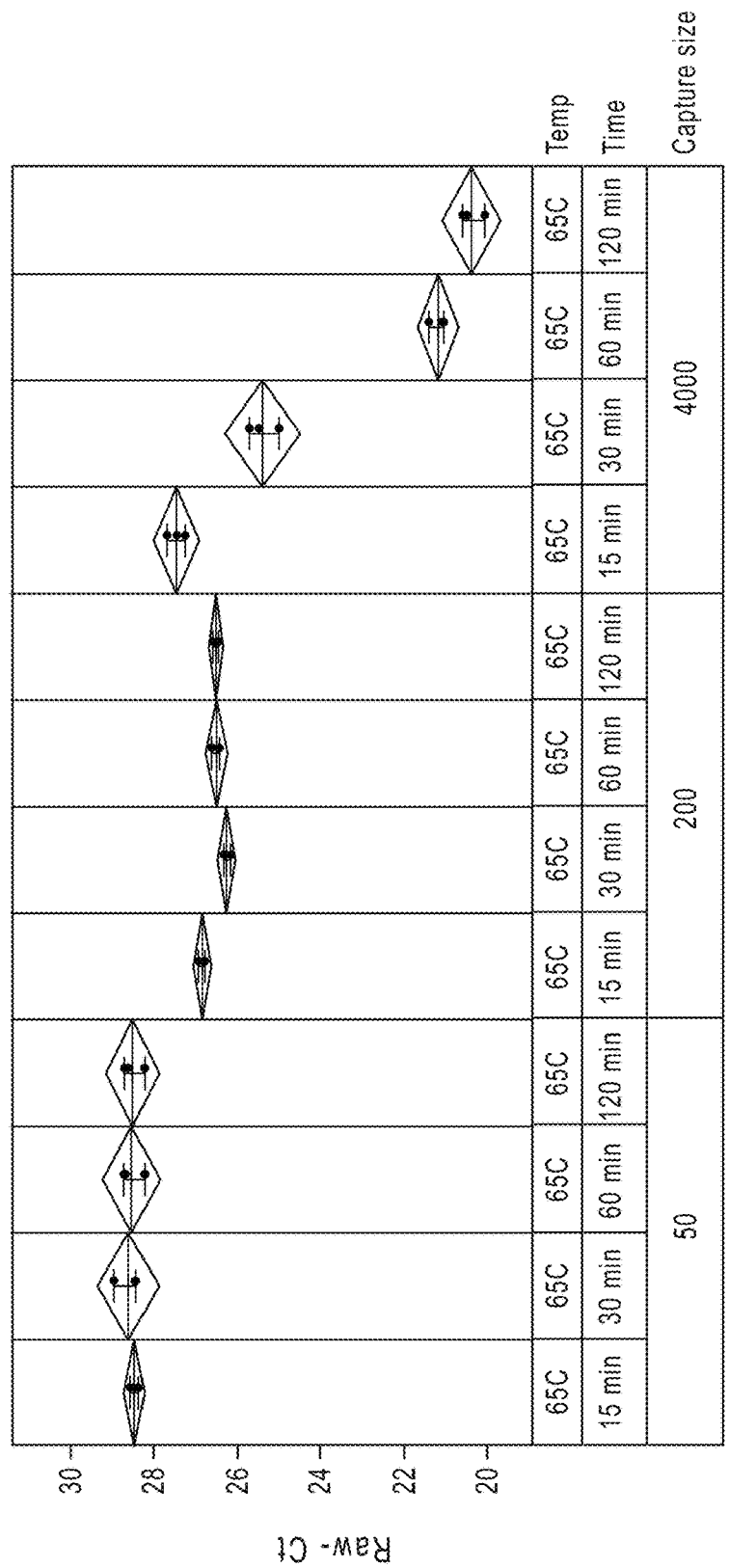
Figure 23:
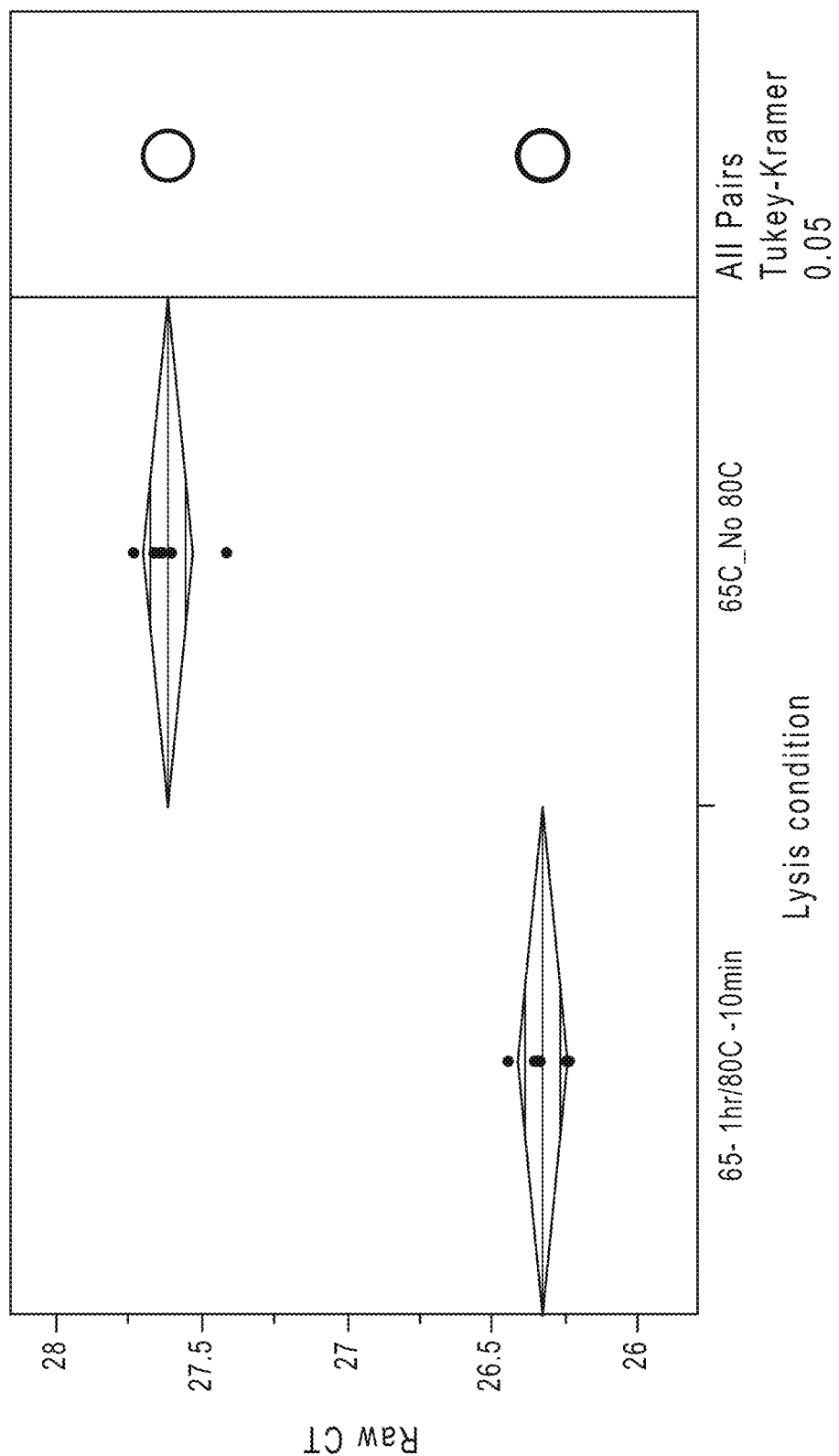
Figure 24:
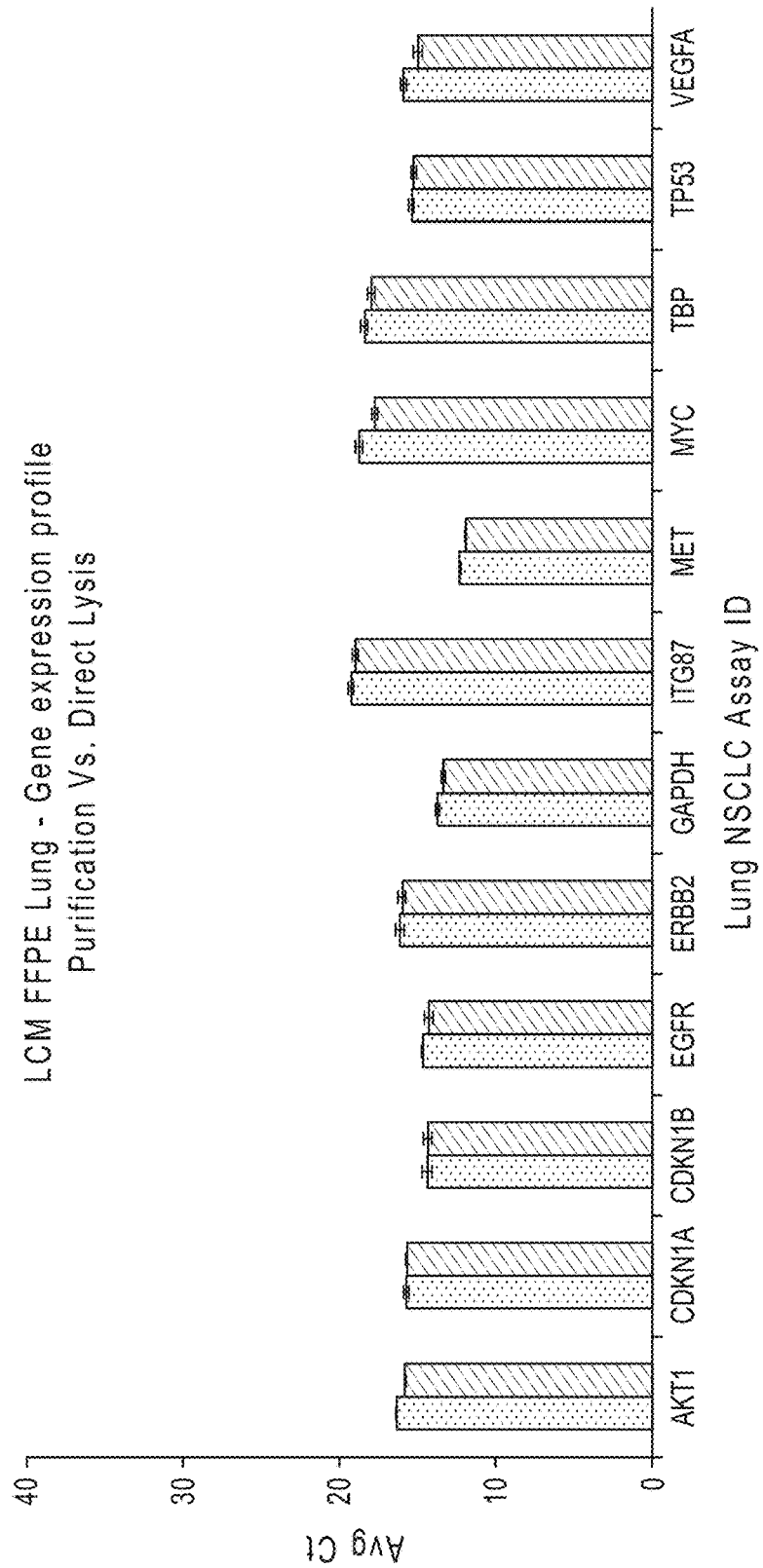

Referring to FIGS. 14-16, results of RNA qPCR experiments are demonstrated:
FFPE breast tissue lysate was incubated at temperature mentioned in the table.
Lysate buffer used: Cells to Ct buffer
After 1 hour incubation reaction (for each time point) Lysate was treated with DNase
Reaction was stopped by adding stop solution
Sample was assessed by RT-PCR assay Referring to FIGS. 17-19, results of DNA qPCR experiments are demonstrated:
FFPE breast tissue lysate was incubated at temperature mentioned in the table.
Lysate buffer used: Cells to Ct buffer
After 1 hour incubation reaction (for each time point) Lysate was treated with RNase
Reaction was stopped by adding stop solution
Sample was assessed by PCR assay Regarding FIGS. 16 and 19:
Boundary test for 65 C: Sample lysates were tested at ±1 C (64 C and 66 C).
Tukey Kramer analysis indicated that there is no significant difference between 64 C, 65 C and 66 C for both DNA and RNA yield. (circles overlapping—no significant difference)

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

The following United States Patents are all herein incorporated by reference in their entirety:

| | | | | |
|---|---|---|---|---|
| U.S. Pat. No. 5,859,699; | U.S. Pat. No. 6,690,470; | U.S. Pat. No. 7,456,938; | U.S. Pat. No. 7,964,350; | U.S. Pat. No. 8,828,664; |
| U.S. Pat. No. 6,157,306; | U.S. Pat. No. 6,887,703; | U.S. Pat. No. 7,473,401; | U.S. Pat. No. 8,288,406; | U.S. Pat. No. 9,279,152. |
| U.S. Pat. No. 6,469,779; | U.S. Pat. No. 7,049,558; | U.S. Pat. No. 7,556,733; | U.S. Pat. No. 8,346,483; | |
| U.S. Pat. No. 6,495,195; | U.S. Pat. No. 7,075,640; | U.S. Pat. No. 7,749,388; | U.S. Pat. No. 8,715,955; | |
| U.S. Pat. No. 6,528,248; | U.S. Pat. No. 7,229,595; | U.S. Pat. No. 7,776,273; | U.S. Pat. No. 8,722,357; | |

What is claimed is:

1. A method for processing a sample containing one or more nucleic acids, comprising:
   selecting a sample from a biological specimen or heterogeneous mixture of biological cells using an optical system, wherein the selected sample is in contact with a first surface of a first substrate and the biological specimen or heterogeneous mixture of biological cells is in contact with a second substrate comprising a second surface;
   moving the first substrate away from the second surface such that the selected sample maintains contact with the first surface and the selected sample does not maintain contact with the second surface;
   attaching the first substrate to a container such that the selected sample is disposed within an internal volume of the container; and
   forming a sample solution within the internal volume of the container by contacting the selected sample with a lysis mixture using a protocol.

2. The method according to claim 1, wherein the optical system comprises is a microscope.

3. The method according to claim 1, wherein the optical system comprises a laser capture microdissection apparatus.

4. The method according to claim 1, wherein transferring the selected sample comprises:
   levitating the selected sample into the container; or
   using gravity to move the selected sample from the first substrate to the container.

5. The method according to claim 1, further comprising detaching the first substrate from the container.

6. The method according to claim 1, wherein the first substrate comprises one or more of a laser capture microdissection cap (LCM cap), a sample carrier, or an extraction device.

7. The method according to claim 1, wherein the container comprises a container cap and transferring the selected sample comprises transferring the selected sample from the first substrate to the container cap.

8. The method according to claim 1, wherein the container comprises a well or vial of a microtiter plate and the first substrate is attached to the well or vial to form the internal volume.

9. The method of claim 8, further comprising a plurality of additional substrates that are geometrically similar or equivalent to the first substrate, wherein each of the substrates is attached to one of the wells of the microtiter plate.

10. The method of claim 8, wherein the microtiter plate comprises 96 wells.

11. The method according to claim 1, wherein the container is a first container, the method further comprising attaching the first substrate to the first container to provide a first closed container.

12. The method according to claim 11, further comprising at least one of placing the first closed container on a holder and/or placing the first closed container in an incubator.

13. The method of claim 12, further comprising a plurality of additional closed containers, each additional closed container comprising an additional substrate and an additional container that are geometrically similar or equivalent to the first substrate and the first container, wherein the first closed container and the additional closed containers are together placed on the holder and/or placed in the incubator.

14. The method according to claim 1, wherein the protocol comprises heating the sample solution to a first temperature that is greater than 37 degrees Celsius and less than or equal to 75 degrees Celsius.

15. The method according to claim 1, wherein the protocol comprises heating the sample solution to a first temperature that is greater than or equal to 45 degrees Celsius and less than or equal to 75 degrees Celsius.

16. The method according to claim 1, further comprising performing an assay, experiment, or test on the sample containing one or more nucleic acids.

17. The method according to claim 16, wherein the assay, experiment, or test on the sample containing one or more nucleic acids is performed without filtration, purification, or pipetting of the sample solution.

18. The method according to claim 16, wherein performing an assay, experiment, or test on the sample containing one or more nucleic acids comprises sequencing the one or more nucleic acids.

19. The method according to claim 16, wherein performing an assay, experiment, or test on the sample containing one or more nucleic acids includes performing a polymerase chain reaction (PCR) assay, experiment or test on one or more nucleic acids.

* * * * *